US011887719B2

(12) United States Patent
Salehian et al.

(10) Patent No.: US 11,887,719 B2
(45) Date of Patent: Jan. 30, 2024

(54) FOOD KNOWLEDGE GRAPH FOR A HEALTH TRACKING SYSTEM

(71) Applicant: MYFITNESSPAL, INC., San Francisco, CA (US)

(72) Inventors: Hesamoddin Salehian, San Francisco, CA (US); Poojit Sharma, San Francisco, CA (US); Kent Frazier, San Francisco, CA (US); Surender Reddy Yerva, San Francisco, CA (US); Iman Barjasteh, San Francisco, CA (US); Layla Martin, San Francisco, CA (US)

(73) Assignee: MyFitnessPal, Inc., Austin, TX (US)

( * ) Notice: Subject to any disclaimer, the term of this patent is extended or adjusted under 35 U.S.C. 154(b) by 909 days.

(21) Appl. No.: 16/417,291

(22) Filed: May 20, 2019

(65) Prior Publication Data

US 2019/0355465 A1 Nov. 21, 2019

Related U.S. Application Data

(60) Provisional application No. 62/674,170, filed on May 21, 2018.

(51) Int. Cl.
G16H 20/60 (2018.01)
G09B 19/00 (2006.01)
G06N 5/02 (2023.01)

(52) U.S. Cl.
CPC .............. *G16H 20/60* (2018.01); *G06N 5/02* (2013.01); *G09B 19/0092* (2013.01)

(58) Field of Classification Search
CPC ........ G16H 10/00–80/00; G06N 3/00–99/007; G09B 1/00–29/14
See application file for complete search history.

(56) References Cited

U.S. PATENT DOCUMENTS 6,478,736 B1    11/2002   Mault
7,966,291 B1     6/2011   Petrovic
(Continued)

FOREIGN PATENT DOCUMENTS

EP         1758038 A1 *   2/2007  ......... G06F 19/3475
WO   2007023619 A1     3/2007
(Continued)

OTHER PUBLICATIONS

Schumer et al., "Evaluating the Dietary and Nutritional Apps in the Google Play Store," Healthc Inform Res. Jan. 2018; 24(1):38-45. (Year: 2018).*

(Continued)

*Primary Examiner* — Jonathon A. Szumny
(74) *Attorney, Agent, or Firm* — Maginot, Moore & Beck, LLP

(57) ABSTRACT

A method of operating a health tracking system is disclosed. The method comprises: storing a food knowledge graph having a plurality of labels describing consumable items and a plurality of relationships between pairs of labels, some of the labels being generic names for consumable items; receiving a data record having a descriptive string regarding a consumable item from a first health tracking device; matching the descriptive string to at least one label in the plurality of labels; and updating one or more information fields of the data record to associate the data record with the at least one label to which the descriptive string was matched. In some embodiments, the method further includes receiving a request for data records from a health tracking device and matching the request to the plurality of labels to provide an improved response to the request for data records.

13 Claims, 18 Drawing Sheets

(56) References Cited

U.S. PATENT DOCUMENTS

| | | | |
|---|---|---|---|
| 9,311,568 B1 | 4/2016 | Feller | |
| 9,797,873 B1* | 10/2017 | Feller | G01N 33/00 |
| 9,824,152 B1* | 11/2017 | Feller | G06F 16/9535 |
| 10,480,990 B1* | 11/2019 | Wallace | G09B 5/04 |
| 10,825,567 B1* | 11/2020 | Wala | G16H 10/20 |
| 11,062,620 B1* | 7/2021 | Wallace | G09B 19/0092 |
| 2003/0132298 A1* | 7/2003 | Swartz | G07G 1/0072 |
| | | | 235/472.02 |
| 2004/0194141 A1 | 9/2004 | Sanders | |
| 2007/0118405 A1 | 5/2007 | Campbell | |
| 2008/0040313 A1 | 2/2008 | Schachter | |
| 2008/0091705 A1 | 4/2008 | McBride | |
| 2009/0099873 A1 | 4/2009 | Kurple | |
| 2010/0161432 A1* | 6/2010 | Kumanov | G06Q 20/102 |
| | | | 705/40 |
| 2010/0169361 A1 | 7/2010 | Chen | |
| 2011/0119161 A1 | 5/2011 | Van Treeck | |
| 2011/0282861 A1* | 11/2011 | Bergstraesser | G06F 16/24564 |
| | | | 707/E17.014 |
| 2011/0318717 A1* | 12/2011 | Adamowicz | G16H 20/60 |
| | | | 434/127 |
| 2012/0005222 A1 | 1/2012 | Bhagwan | |
| 2012/0023107 A1 | 1/2012 | Nachnani | |
| 2013/0216982 A1 | 8/2013 | Bennett | |
| 2014/0081772 A1* | 3/2014 | Luke | G06Q 30/08 |
| | | | 705/14.71 |
| 2014/0147829 A1 | 5/2014 | Jerauld | |
| 2014/0324607 A1 | 10/2014 | Frehn | |
| 2015/0228062 A1 | 8/2015 | Joshi | |
| 2015/0235136 A1 | 8/2015 | Dillon | |
| 2015/0242468 A1* | 8/2015 | Shoemaker | G06F 40/284 |
| | | | 707/755 |
| 2015/0276700 A1 | 10/2015 | Goel | |
| 2016/0012749 A1 | 1/2016 | Connor | |
| 2016/0103910 A1 | 4/2016 | Kim et al. | |
| 2017/0046980 A1* | 2/2017 | Mehta | G09B 19/0092 |
| 2017/0053362 A1 | 2/2017 | Galarraga | |
| 2018/0240359 A1* | 8/2018 | Hujsak | G06N 20/00 |
| 2019/0006040 A1* | 1/2019 | Fleming | G09B 19/0092 |
| 2019/0103173 A1* | 4/2019 | Power | H04L 67/12 |
| 2019/0188776 A1* | 6/2019 | Hammond | G06Q 30/0633 |
| 2019/0228039 A1* | 7/2019 | Doble | G06F 16/2282 |
| 2019/0286656 A1* | 9/2019 | Yerva | G16H 20/60 |
| 2020/0242964 A1* | 7/2020 | Wu | G06F 16/9535 |
| 2020/0365250 A1* | 11/2020 | Kim | G06Q 30/0185 |
| 2022/0093234 A1* | 3/2022 | Shima | G16H 20/60 |

FOREIGN PATENT DOCUMENTS

| | | | | |
|---|---|---|---|---|
| WO | WO-2013090768 A2 * | 6/2013 | | G06Q 10/0631 |
| WO | WO-2016202274 A1 * | 12/2016 | | |
| WO | WO-2017015612 A1 * | 1/2017 | | G06K 19/06028 |
| WO | WO-2017085777 A1 * | 5/2017 | | G06Q 30/02 |

OTHER PUBLICATIONS

Franco et al., "Popular Nutrition-Related Mobile Apps:A Feature Assessment," JMIR Mhealth Uhealth 2016;4(3):e85 (Year: 2016).*

Hochuli, Alexandra, Data Cleansing for Food Composition Data, Global Information Systems Group, 2014.

* cited by examiner

FOOD KNOWLEDGE GRAPH FOR A HEALTH TRACKING SYSTEM

CROSS-REFERENCE TO RELATED APPLICATIONS

This disclosure claims priority to U.S. Provisional Patent Application Ser. No. 62/674,170, filed May 21, 2018, the entire contents of which are incorporated by reference herein.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The methods and systems disclosed in this document relate health tracking systems having a food database and, more particularly, to a food knowledge graph for supplementing the food database.

BACKGROUND

In recent years, health and fitness tracking applications that track food consumption have become very popular. Food consumption is important to a healthy lifestyle and a person's diet is well known to be related to various health conditions, such as diabetes and obesity to name a few. These applications enable users to gain insights that help them make smarter choices and create healthier habits. In order to track food consumption, such health and fitness tracking applications typically utilize a large crowdsourced database of foods and beverages that can be logged by users. The largest databases include records having nutritional information for millions of foods and beverages. However, these records generally include very minimal information about the food, which is often limited to nothing more than a basic user-generated text description and basic nutritional content information. Accordingly, user interaction with the database is often limited to basic text searching of the database. As a result, it is often cumbersome for users to find foods and beverages in the database. Accordingly, it would be advantageous to provide users with health tracking systems that includes records having more robust information about foods, thereby enabling more informative, efficient, and diverse user interactions with the database.

SUMMARY

In accordance with one exemplary embodiment of the disclosures, a method of operating a health tracking system is disclosed. The method comprises: storing, with a processor, in a database, a plurality of labels describing consumable items and a plurality of relationships between pairs of labels in the plurality of labels, at least some of the labels in the plurality of labels being generic names for consumable items; receiving, with the processor, a data record comprising at least one descriptive string regarding a first consumable item from a first health tracking device; matching, with the processor, the at least one descriptive string to at least one first label in the plurality of labels; updating, with the processor, at least one information field of the data record to associate the data record with the at least one first label to which the at least one descriptive string was matched; receiving, with the processor, a request for data records from a second health tracking device; matching, with the processor, the request to the at least one first label; and providing, with the processor, the data record having the updated at least one information field to the second health tracking device in response to request being matched to the at least one first label.

Pursuant to another exemplary embodiment of the disclosures, a health tracking system is disclosed. The health tracking system comprises: an interface configured to communicate with a health tracking device of a user; a database configured to store (i) a plurality of labels describing consumable items and a plurality of relationships between pairs of labels in the plurality of labels, at least some of the labels in the plurality of labels being generic names for consumable items, and (ii) a plurality of consumable records, each consumable record including at least a descriptive string regarding a consumable item and each consumable record being associated with at least one label in the in the plurality of labels; and a data processing system in communication with the health tracking device via the interface and the database. The data processing system is configured to: receive a search string from the health tracking device of the user via the interface; match the search string to at least one first label in the plurality of labels; generate a list of consumable records including consumable records in the plurality of consumable records that are associated with the at least one first label to which the search string was matched; and provide the list of consumable records to the health tracking device as search results.

In accordance with yet another exemplary embodiment, a further method of operating a health tracking system is disclosed. The method comprises: storing, with the processor, in a database, (i) a plurality of labels describing consumable items and a plurality of relationships between pairs of labels in the plurality of labels, at least some of the labels in the plurality of labels being generic names for consumable items, and (ii) a plurality of consumable records, each consumable record including at least a descriptive string regarding a consumable item and each consumable record being associated with at least one label in the in the plurality of labels; receiving, with the processor, from a user, at least one consumable item selection corresponding to a consumable record in the plurality of consumable records in the database; identifying, with the processor, at least one first label in the plurality of labels that is associated with the consumable record in the plurality of consumable records corresponding to the at least one consumable item selection; and providing, with the processor, a list of consumable records to the health tracking device as recommended consumable items for the user based on the at least one first label.

These and other aspects of the disclosure shall become apparent when considered in light of the disclosure provided herein.

BRIEF DESCRIPTION OF THE DRAWINGS

The foregoing aspects and other features of a health tracking system are explained in the following description, taken in connection with the accompanying drawings.

Figure 1:
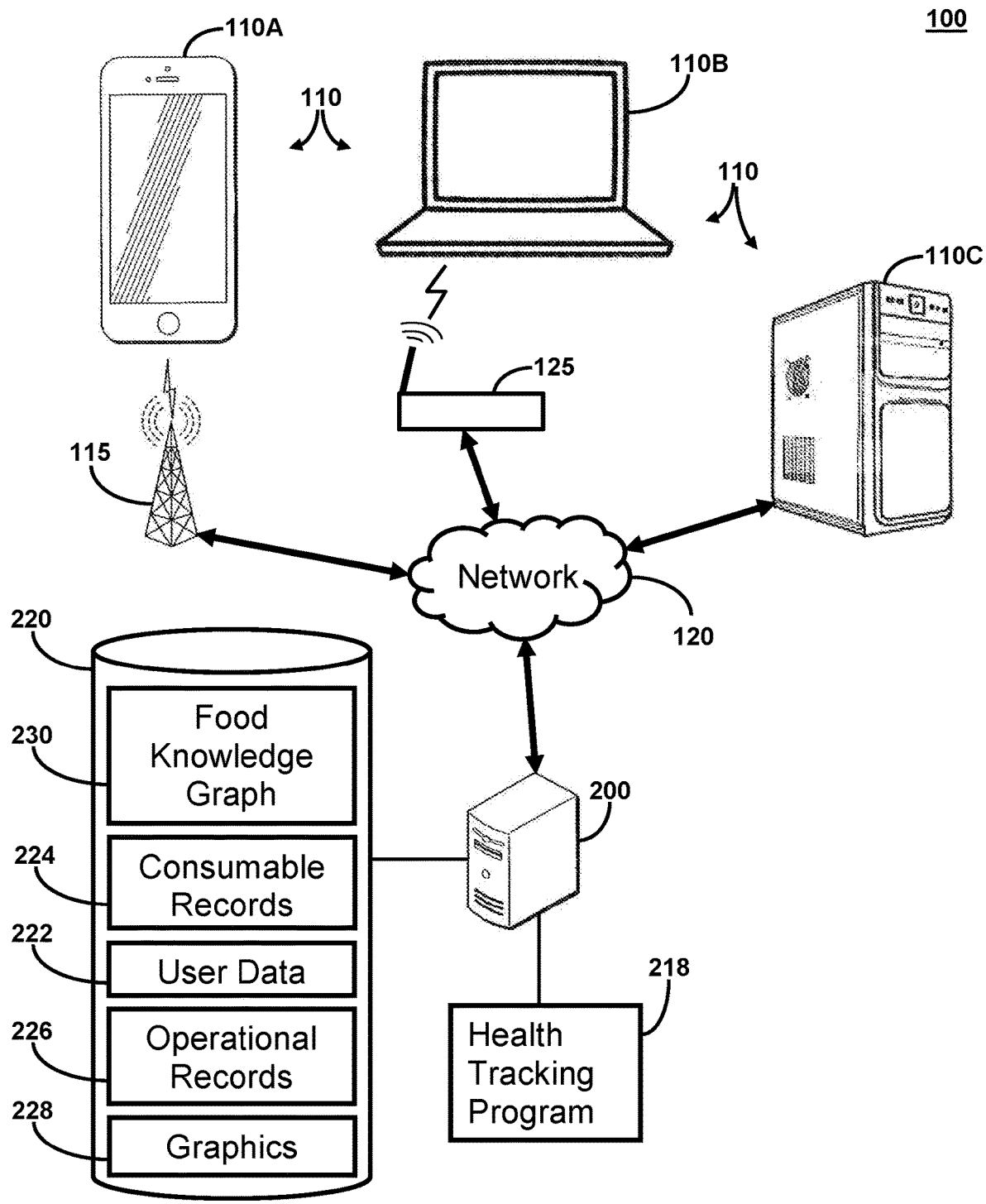
FIG. 1 shows a health tracking system.

All Figures © Under Armour, Inc. 2018. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As used herein, the term "consumable" or "consumable item" refers to foods, beverages, dietary supplements, vitamin supplements, medication, and other items for consumption. As used herein, the term "consumable record" or "consumable item record" refers to a database record that relates to a particular consumable. Each consumable record comprises a plurality of data fields that relate to a particular consumable item. In some embodiments, each consumable record includes a description field that includes data, such as a text string, that identifies or describes the particular consumable. In some embodiments, each consumable record includes a brand field that includes data, such as a text string, that identifies or describes the brand of the particular consumable. In some embodiments, each consumable record includes an ingredients field that includes data, such as one or more text strings, that list ingredients for a particular consumable. In some embodiments, each consumable record includes fields for caloric content, macronutrients, micronutrients, serving size, and other nutrition and health information.

Health Tracking System

With reference to FIG. 1, an exemplary embodiment of a health tracking system 100 that utilizes a food knowledge graph to provide to provide structured and detailed knowledge about consumables is shown. In the illustrated embodiment, the health tracking system 100 includes a plurality of health tracking devices 110 in communication with a system server 200 or other data processing system over a network 120 such as, e.g. the Internet.

The server 200 comprises a computerized device or data processing system configured to run one or more software applications on a processor thereof (e.g. the network-side health tracking program 218). The server 200 of the present embodiment is further configured to receive a plurality of consumable records which include item descriptions, as well as caloric and nutritional contents of a respective plurality of consumable items which are entered at the health tracking devices 110, other consumer devices, and/or provided from one or more manufacturing or distributing entities. The consumable records are stored at a storage apparatus or memory of the server 200 (e.g., consumable records 224).

The storage apparatus or memory is configured to store instructions including a network-side health tracking program 218 (which may also be referred to herein as the "health tracking application"), as well as a database 220 accessible by at least the health tracking program 218. The database 220 includes user data 222, consumable records 224, operational records 226, and graphics 228. Alternatively, the server 200 may be in communication with a separate storage entity (not shown) for storage thereof.

As will be discussed in further detail elsewhere herein, the server 200 utilizes a food knowledge graph 230, which is also included in the database 220, to provide structured and detailed knowledge about consumables to which the consumable records 224 correspond. In one embodiment, the food knowledge graph 230 is used to generate additional metadata which is included in the consumable records 224, in addition to the basic data entered by a user upon creation each consumable record. In one embodiment, the food knowledge graph 230 is used to provide more relevant search results when a user searches the consumable records 224. In one embodiment, the food knowledge graph 230 is used to provide more relevant recommendations of consumable records 224 to the user.

The health tracking devices 110 (which may also be referred to herein as "health and fitness tracking devices") comprise any number of computerized apparatus, which include a user interface, such as e.g., a smartphone 110A, laptop computer 110B, a tablet computer, a smart watch, a desktop computer 110C, or other such device. In at least one embodiment, the user interface may comprise an LCD touch screen or the like, a mouse or other pointing device, a keyboard or other keypad, speakers, and a microphone, as will be recognized by those of ordinary skill in the art. The user interface provides the user with any of various health, fitness and activity related data such as food and nutritional consumption, calorie expenditure, sleep metrics, weight, body fat, heart rate, distance travelled, steps taken, etc. In order to connect to the network 120, the health tracking devices 110 are generally configured to utilize any of various wired or wireless communications components, infrastructures and systems, such as cell towers 115 of a mobile telephony network, wireless routers 125, Bluetooth®, near field communication (NFC), or physical cables. Health tracking devices 110 may use data collected from sensors associated to or in communication with the health tracking device 110, such as heart rate monitors, step counters, stair counters, global positioning system ("GPS") tracking devices, as well as various other motion tracking and biometric monitoring devices. Alternatively, or in addition, a user may manually enter health related data. Such sensors allow the user to easily track and automatically log activity and/or consumption information with the health tracking device. In addition, the health tracking device 110 may include one or more cameras configured to obtain health parameter data including e.g., capture images of a user's performance of an activity and/or capture images of consumed items or descriptions thereof (including barcodes or other machine readable identifiers).

The health tracking devices 110 are configured to communicate with the system server 200 in order to enable: accessing and searching of the consumable records 224 stored thereat, display of the consumable records, provide additional records, and/or enable the user to select individual ones of the displayed consumable records for the purposes of caloric and nutritional logging. In one embodiment, foregoing functions are performed via execution of one or more software applications at the server 200 (i.e., server or network-side applications) in communication with one or more complementary software applications at the health tracking devices 110 (i.e., client-side applications). For example, the health tracking program 218, running on the processor (of the server 200) may be utilized to accomplish the foregoing, as explained in further detail below. A client-side software application for performing various functions necessary for the herein disclosed concepts may also be utilized (see health tracking application 316 of FIG. 3, discussed below).

System Server

Figure 2:
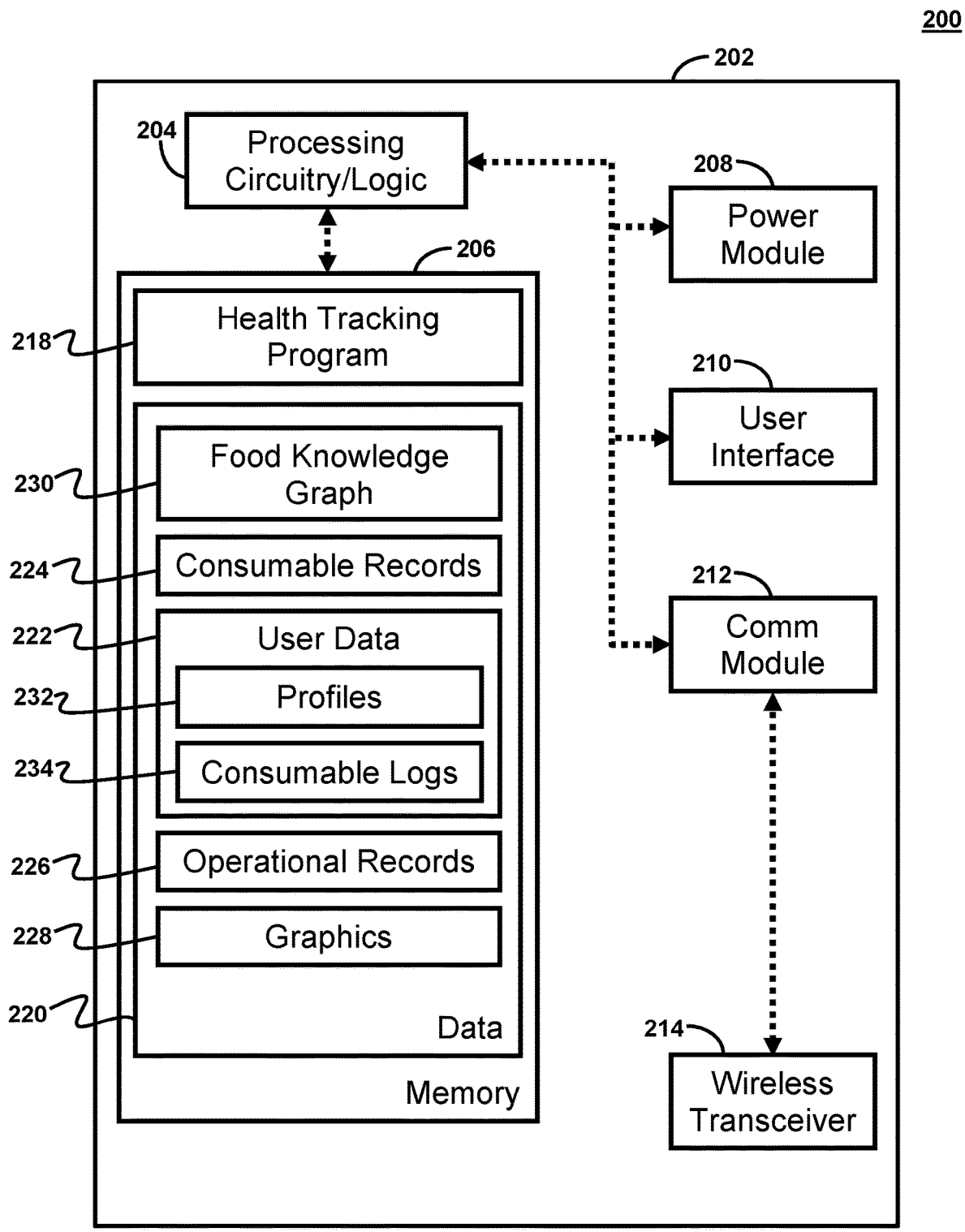
FIG. 2 shows a system server or data processing system of the health tracking system.

With reference now to FIG. 2, a block diagram of an exemplary embodiment of the system server 200 of FIG. 1 is shown. It is appreciated that the embodiment of the system server 200 shown in FIG. 2 is only one exemplary embodiment of a system server 200. As such, the exemplary embodiment of the system server 200 of FIG. 2 is merely representative of any of various manners or configurations of system servers or other data processing systems that are operative in the manner set forth herein.

The system server 200 of FIG. 2 is typically provided in a housing, cabinet or the like 202 that is configured in a typical manner for a server or related computing device. In one embodiment, the system server 200 includes processing circuitry/logic 204, memory 206, a power module 208, a user interface 210, a network communications module 212, and a wireless transceiver 214.

The processing circuitry/logic 204 is operative, configured and/or adapted to operate the system server 200 including the features, functionality, characteristics and/or the like as described herein. To this end, the processing circuitry/logic 204 is operably connected to the memory 206, the power module 208, the user interface 210, the network communications module 212, and the wireless transceiver 214. The memory 206 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. The memory 206 is configured to store instructions including a network-side health tracking application 218 for execution by the processing circuitry/logic 204, as well as a database 220 for use by at least the health tracking program 218. The database 220 includes user data 222, consumable records 224, operational records 226, graphics 228, and the food knowledge graph 230. As discussed in greater detail below, the health tracking application 218 includes instructions for utilizing the food knowledge graph 230 to provide more informative, efficient, and diverse user interactions with consumable records 224 in the database 220.

With continued reference to FIG. 2, the power module 208 of the system server 200 is operative, adapted and/or configured to supply appropriate electricity to the system server 200 (i.e., including the various components of the system server 200). The power module 208 may operate on standard 120 volt AC electricity, but may alternatively operate on other AC voltages or include DC power supplied by a battery or batteries.

The network communication module 212 of the system server 200 provides an interface that allows for communication with any of various devices using various means. In particular, the network communications module 212 includes a local area network port that allows for communication with any of various local computers housed in the same or nearby facility. In some embodiments, the network communications module 212 further includes a wide area network port that allows for communications with remote computers over the Internet (e.g., network 120 of FIG. 1). Alternatively, the system server 200 communicates with the network 120 via a modem and/or router of the local area network. In one embodiment, the network communications module is equipped with a wireless transceiver 214 or other wireless communications device. Accordingly, it will be appreciated that communications with the system server 200 may occur via wired communications or via the wireless communications. Communications may be accomplished using any of various known communications protocols. In the embodiment of FIG. 2, the wireless transceiver 214 may be a Wi-Fi transceiver, but it will be recognized that the wireless transceiver may alternatively use a different communications protocol.

The system server 200 may be accessed locally by an authorized user (i.e., an administrator or operator). To facilitate local access, the system server 200 includes an interactive user interface 210. Via the user interface 210, an operator may access the instructions, including the health tracking application 218, and may collect data from and store data to the memory 206. In at least one embodiment, the user interface 210 may suitably include an LCD touch screen or the like, a mouse or other pointing device, a keyboard or other keypad, speakers, and a microphone, as will be recognized by those of ordinary skill in the art. Accordingly, the user interface 210 is configured to provide an administrator or other authorized user with access to the memory 206 and allow the authorized user to amend, manipulate and display information contained within the memory.

As mentioned above, the memory 206 includes various programs and other instructions that may be executed by the processor circuitry/logic 204. In particular, the memory 206 of the system server 200 of FIG. 2 includes the health tracking program 218 (which may also be referred to herein as a "health tracking application"). The health tracking program 218 is configured to cause the system server 200 to enable a user to obtain nutritional data related to any of various consumables. Execution of the health tracking application 218 by the processor circuitry/logic 204 results in signals being sent to and received from the user interface 210 and the communications module 212 (for further delivery to a user device such as a health tracking device 110), in order to allow the user receive and update various aspects of the consumable records 224. The network-side health tracking application 218 is configured to provide various graphical views and screen arrangements to be displayed to a user on a health tracking device 110.

The user data 222 includes at least user profiles 232 and corresponding consumable logs 234. The user profiles 232 include a profile data for each user of the health tracking system 100. Each user profile includes demographic information for the users such as name, age, gender, height, weight, performance level (e.g., beginner, intermediate, professional, etc.) and/or other information for the user. In at least one embodiment, the consumable logs 234 include a consumable diary/log for each user (which may also be referred to herein as a "food diary"). The consumable diary/log allows the user to track consumables that are consumed by the user over a period of days and any nutritional data associated with the food consumed. For example, the consumable diary/log may allow the user to enter particular consumable that is consumed by the user and keep track of the associated calories, macronutrients, micronutrients, sugar, fiber, and/or any of various other nutritional data associated with the consumables entered by the user in the consumable diary/log. In some embodiments, the user data 222 further includes various activity and fitness data collected by sensors (not shown) associated with the health tracking devices 110.

In an alternative embodiment, the foregoing profile data may be stored at a storage entity separate from yet in communication with the server 200. For example, a centralized server may be provided which is configured to store all data relating to an individual user in one storage area (including workout data, nutrition/consumption data, profile data, etc.).

A plurality of consumable records 224 is stored in the database 220. As discussed above, the term "consumable record" refers to a database record that relates to a particular consumable item. In at least one embodiment, each consumable record comprises a plurality of data fields that relate to a particular consumable item. In the disclosed embodiment, each of the consumable records includes a number of fields including, for example, a name for the consumable item, summary information about the consumable item, and detailed nutritional information about the consumable item. Detailed nutritional information about a consumable item may include one or more of: serving size, calories, nutrients, ingredients, or any other nutritional information about the item. For example, the detailed nutritional information may include information that may be provided on USDA food labels or state-regulated food labels (e.g., vitamin and mineral content, fat content, cholesterol content, protein content, sugar content, carbohydrate content, fiber content, organic contents, etc.). The summary information about the consumable may include some subset of the more detailed information about the consumable. For example, the summary information about the consumable may only include serving size and calorie information. The various fields of each consumable record may be populated by data from any user or third party data providers. Many, if not all, of consumable records 224 are created by users of the health tracking system 100 and/or have fields that are editable by users, without the need for special authorization or privileges. However, it will be recognized that in at least some embodiments, consumable records 224 may have been entered by any of various sources including an administrator or operator of the health tracking system 100, commercial food providers (e.g., food distributors, restaurant owners, etc.), and/or users of the health tracking system 100. In addition, certain information may be stored in a machine readable code (such as a bar code or QR code) which is captured via a camera or other scanner at the user device 110.

The operational records 226 include current and historical data stored by the system server 200 in association with operation of the system server 200, execution of the health tracking application 218, and/or manipulation of the database 220 within the memory 206. For example, the operational records 226 may include information concerning amendments made to any of various consumable records 224. The operational records 226 may also include other information related to the control and operation of the system server 200, including statistical, logging, licensing, and historical information.

In one embodiment, graphical views 228 are provided at the server 200 which are pushed to the health tracking device 110 for display thereat of various screen arrangements.

While the system server 200 has been explained in the foregoing embodiment as housing the health tracking program 218 and the various records and databases in the memory 206, it will be recognized that in other embodiments these components may be retained in other one or more remote locations in communication with the health tracking system 100. For example, in at least one embodiment, the consumable records 224 may comprise data retained by a database separate from the system server 200. Alternatively, the consumable records 224 or certain fields of the consumable records 224 are received from a third party database. In such embodiments, the health tracking application may utilize any number of application programming interfaces (APIs) to access the data in the third party databases and incorporate such information for use in the health tracking application 218, without local storage thereof. Accordingly, it will be recognized that the description of the system server 200 of FIG. 2 is but one exemplary embodiment of a data processing system that may be utilized by the health tracking system 100.

A computer program product implementing an embodiment disclosed herein may therefore comprise one or more computer-readable storage media storing computer instructions executable by a processor to provide an embodiment of a system or perform an embodiment of a method disclosed herein. Computer instructions (e.g., the health tracking application 218) may be provided by lines of code in any of various languages as will be recognized by those of ordinary skill in the art. A "non-transitory computer-readable medium" may be any type of data storage medium that may store computer instructions, including, but not limited to a memory card, ROM, RAM, write-capable memories, read-only memories, hard drives, discs, flash memory, or any of various other computer-readable medium.

Health Tracking Devices

With reference again to FIG. 1, the health tracking devices 110 may be provided in any of various forms. Examples of a health tracking devices 110 configured for use with the health tracking system 100 include a smartphone 110A, a laptop computer 110B, and a desktop computer 110C, as shown in FIG. 1, as well as various other electronic devices. Accordingly, it will be recognized that the health tracking devices 110 may comprise portable electronic devices such as the smartphone 110A or the laptop computer 110B, or stationary electronic devices such as the desktop computer 110C. Other examples of health tracking devices include, handheld or tablet computers, smart watches, portable media players, other wearable devices, or any of various other health tracking devices configured to receive entry of consumables (not shown).

In one embodiment, data entered at one device 110 may be provided to other ones of the user's devices 110. For example, data entered at the smart phone 110A may be provided to the desktop computer 110C and/or the laptop computer 110B for storage thereat. Alternatively or in addition, the data may be stored at a single network storage apparatus (not shown) having a dedicated portion of storage for records relating to the user and accessible by all of the user's devices 110.

Figure 3:
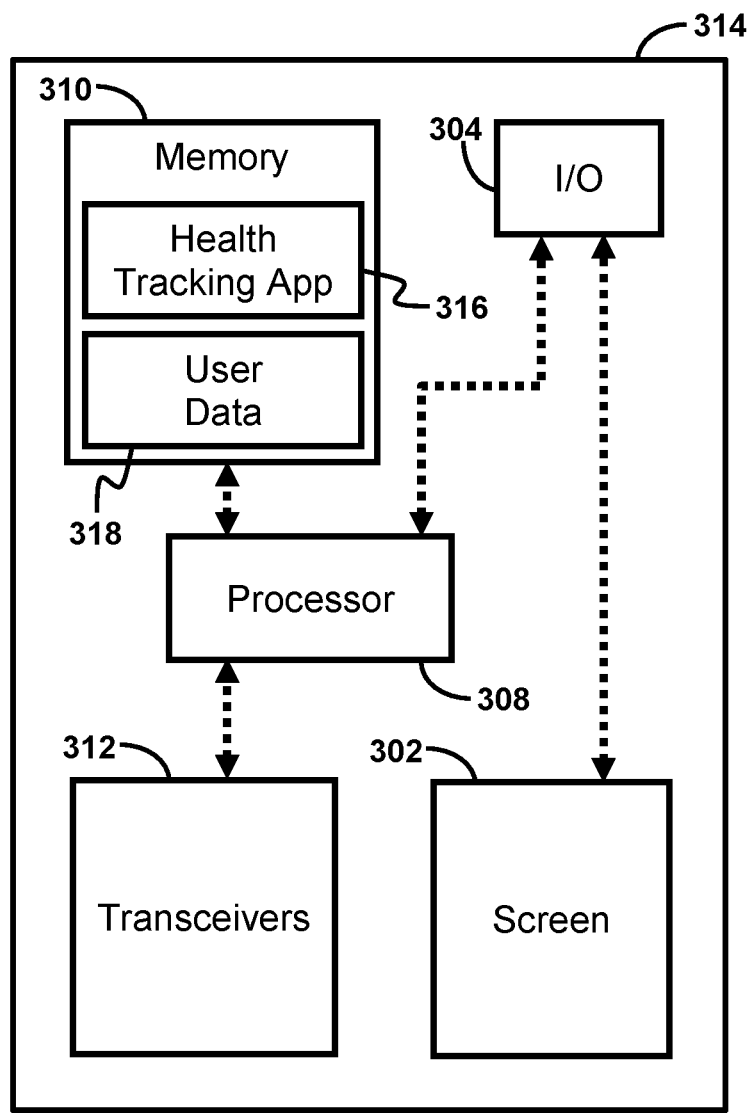
FIG. 3 shows a smart phone of the health tracking system.

With reference now to FIG. 3, in at least one embodiment the health tracking device 110 is provided in the form of a smartphone 110A. The smartphone 110A includes a display screen 302, an input/output (I/O) interface 304, a processor 308, a memory 310, and one or more transceivers 312. The smartphone 110A also includes a protective outer shell or housing 314 designed to retain and protect the electronic components positioned within the housing 314. The smartphone 110A also includes a battery (not shown) configured to power the display screen 302, processor 308, transceivers 312 and various other the electronic components within the smartphone 110A.

The display screen 302 of the smartphone 110A may be an LED screen or any of various other screens appropriate for the personal electronic device. The I/O interface 304 of the smartphone 110A includes software and hardware configured to facilitate communications with the user. The I/O interface 304 is in communication with the display screen 302 and is configured to visually display graphics, text, and other data to the user via the display screen 302. As will be recognized by those of ordinary skill in the art, the components of the health tracking device 110 may vary depending on the type of display device used. Alternative health tracking devices, such as the laptop 110B and the desktop 110C, may include much of the same functionality and components as the smartphone 110A shown in FIG. 3, but may not include all the same functionality or components and/or may include others not listed.

The processor 308 of the smartphone 110A may be any of various processors as will be recognized by those of ordinary skill in the art. The processor 308 is in communication with the I/O interface 304, the memory 310, and the transceivers 312, and is configured to deliver data to and receive data from each of these components. The memory 310 is configured to store information, including data and instructions for execution by the processor 308. It will be recognized by those of ordinary skill in the art that a "processor" includes any hardware system, hardware mechanism or hardware component that processes data, signals or other information. A processor may include a system with a central processing unit, multiple processing units, dedicated circuitry for achieving functionality, or other systems.

The transceivers 312 may be any of various devices configured for communication with other electronic devices, including the ability to send communication signals and receive communication signals. The transceivers 312 may include different types of transceivers configured to communicate with different networks and systems. Such transceivers are well known and will be recognized by those of ordinary skill in the art.

In some embodiments, the transceivers 312 include at least one transceiver configured to allow the smartphone 110A to perform wireless communications with the cell towers 115 of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In some embodiments, the transceivers 312 include at least one transceiver configured to allow the smartphone 110A to communicate with any of various local area networks using Wi-Fi, Bluetooth® or any of various other communications schemes.

In some embodiments, the memory 310 includes program instructions for a graphical user interface configured to provide a client-side health tracking application 316. The memory 310 may further be configured to store certain user data 318, such as e.g., user gender, height, weight, user identifier, password, etc. Additionally, health related data (e.g., data collected from one or more sensors and/or manually entered) may be stored. The processor 308 is configured to read the program instructions from the memory 310 and execute the program instructions to provide the health tracking application 316 to the user so for the purpose of performing health and fitness related tasks for the user, including displaying, modifying, and analyzing the user data 318.

In at least one embodiment, the user data 318 includes a plurality of consumable records which serves as a log of consumables that have been consumed by the user for the purpose of caloric and nutritional tracking. That is to say, the client-side health tracking application 316 is configured to display consumable records and enable the user to select consumable records (from a plurality of records accessed via the network 120), those items that correspond to consumables that he or she has consumed are stored at the client-side for the purpose of logging the consumables in this embodiment. In another alternative, such log may be stored remote from the device and/or only kept at the device for a transitory period.

The memory 310 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Alternatively, or in addition, the software (such as e.g., the client side health tracking program 316) may be downloaded from a network location, such as via the Internet.

Food Knowledge Graph

As discussed above, the database 220 includes a food knowledge graph 230, which is utilized by the health tracking application 218 of the server 200 to provide structured and detailed knowledge about consumables to which the consumable records 224 correspond. The food knowledge graph 230 improves upon the health tracking system 100 by enabling more informative, efficient, and diverse user interactions with the consumable records 224 in the database 220.

As used herein, the phrase "food knowledge graph" or "food graph" refers to a dataset including descriptive labels that describe various aspects of one or more consumables, and defined relationships between two or more of the descriptive labels. The descriptive labels may include any label that provides some description or information regarding a consumable. In some embodiments, a food knowledge graph may take the form of one or more lists or tables that define a data tree or data web in which the descriptive labels comprise the nodes of the tree or web and the relationships comprise the connections between the nodes of the tree or web. In one embodiment, a reduced number of self-referential lists or tables, possible a single self-referential list or table, define all of the labels and relationships that form the data tree or data web. In some embodiments, the labels and/or relationships are stored as a list or table of triplets formed as, for example, [label_ID1, relationship_type, label_ID2] where label_ID1 is a first descriptive label or reference thereto, label_ID2 is a second descriptive label or reference thereto, and relationship_type indicates the nature of the relationship. However, the food knowledge graph can take any other suitable form.

Some exemplary descriptive labels that might be included in a food knowledge graph are generic consumable names (e.g., apple, pizza, sandwich, cola, chocolate chip cookie), brand names (e.g., Kraft®, McDonald's®, Pepsi®), categories of consumables (e.g., fruits, grains, spices, condiments), categories of brand names (e.g. restaurant, fast food, grocery store, national food manufacturer, regional/local food manufacturer), allergens (e.g., nuts, gluten, diary), flavors (e.g., bitter, salty, umami/savory, sour, spicy, and sweet), types of cuisine (e.g., Mexican, Chinese, Italian), dietary restriction compliances (e.g., paleo, vegan, vegetarian, kosher, halal), and other miscellaneous useful descriptive labels (e.g., sugar-free, low-carb, organic, cage-free, non-GMO).

Figure 4A:
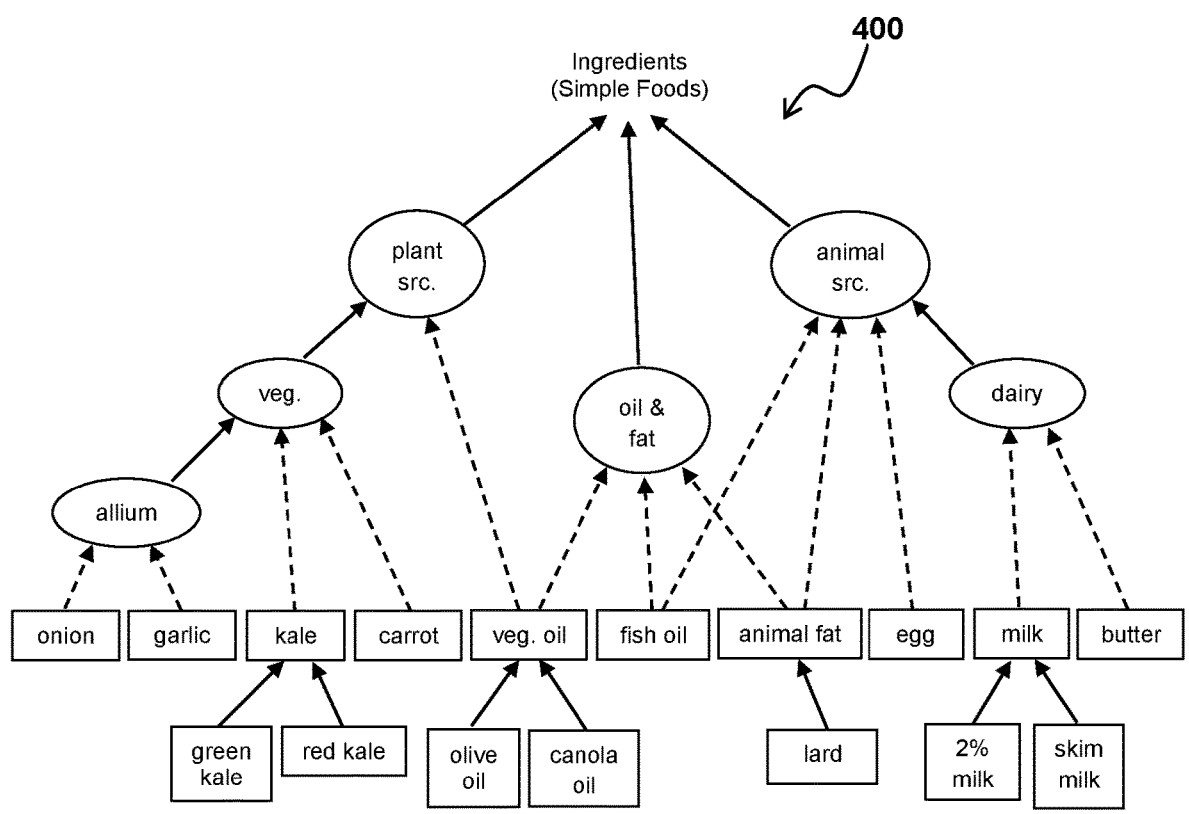
FIG. 4A shows an exemplary partial food knowledge graph illustrating ontological relationships that interconnect consumables names of an ingredient sub-graph.

FIG. 4A shows an exemplary partial food knowledge graph illustrating ontological relationships that interconnect consumables names of an ingredient sub-graph 400. Particularly, one exemplary relationship that might be defined in a food knowledge graph is an ontological relationship ("is a" and/or "has the category") indicating that a first consumable name is a subclass of a second consumable name, or is within a particular category of consumables. For example, a pepperoni pizza "is a" subclass of pizza and an apple "has the category" fruit. Ontological relationships are not, however, limited consumable names. As will be seen below, any type of descriptive label can have similar ontological relationships.

The ingredient sub-graph 400 includes a plurality of generic consumable name labels (indicated by a rectangle) and a plurality of categories of consumables (indicated by an oval). As used herein, "ingredients" (which may also be referred to herein as "simple foods" or "simple consumables") refer to consumables and/or consumable names that are not decomposed into further subcomponents in the food knowledge graph.

The ingredient sub-graph 400 includes a plurality of ontological relationships which indicate that a consumable name is a subclass of another consumable name (indicated by a solid arrow). Particularly, as illustrated in FIG. 4A, the food knowledge graph defines that "green kale" and "red kale" are subclasses of "kale," that "olive oil" and "canola oil" are subclasses of "vegetable oil," that "lard" is a subclass of "animal fat," and that "2% milk" and "skim milk" are subclasses of "milk." Similarly, the ingredient sub-graph 400 further includes a plurality of ontological relationships which indicate that a category of consumable names is a subclass of another category of consumable name (also indicated by a solid arrow). Particularly, as illustrated in FIG. 4A, the food knowledge graph defines that "allium" is a subclass of "vegetable," that "vegetable" is a subclass of "plant source," that "dairy" is a subclass of "animal source," and "plant source," "oil & fat," and that "animal source" are subclasses of "ingredient."

Furthermore, the ingredient sub-graph 400 includes a plurality of ontological relationships which indicate that a consumable name is within a particular category of consumable names (indicated by a dashed arrow). Particularly, as illustrated in FIG. 4A, the food knowledge graph defines that "onion" and "garlic" have the category "allium," that "kale" and "carrot" have the category "vegetable," that "vegetable oil" has the categories "plant source" and "oil & fat," that "fish oil" and "animal fat" have the categories "animal source" and "oil & fat," that "egg" has the category "animal source," and that "milk," and "butter" have the category "dairy."

In the embodiment shown, a particular consumable name is only a direct subclass of a single other consumable name. Furthermore, consumable names are generally only related to the narrowest appropriate category or class. For example "onion" is related to the narrower "allium" category, rather than to the broader "vegetable" or "plant source" categories. In some instances, however, consumable names are related to multiple categories when one category is not strictly a subclass of the other. For example, "vegetable oil" is within both the "plant source" and "oil & fat" categories because "oil & fat" is not strictly a subclass of "plant source" (i.e. consumables in "oil & fat" category could be a "plant source" or an "animal source"). Depending on the design of the sub-graph, different suitable rules for ontological relationships may be applied.

Figure 4B:
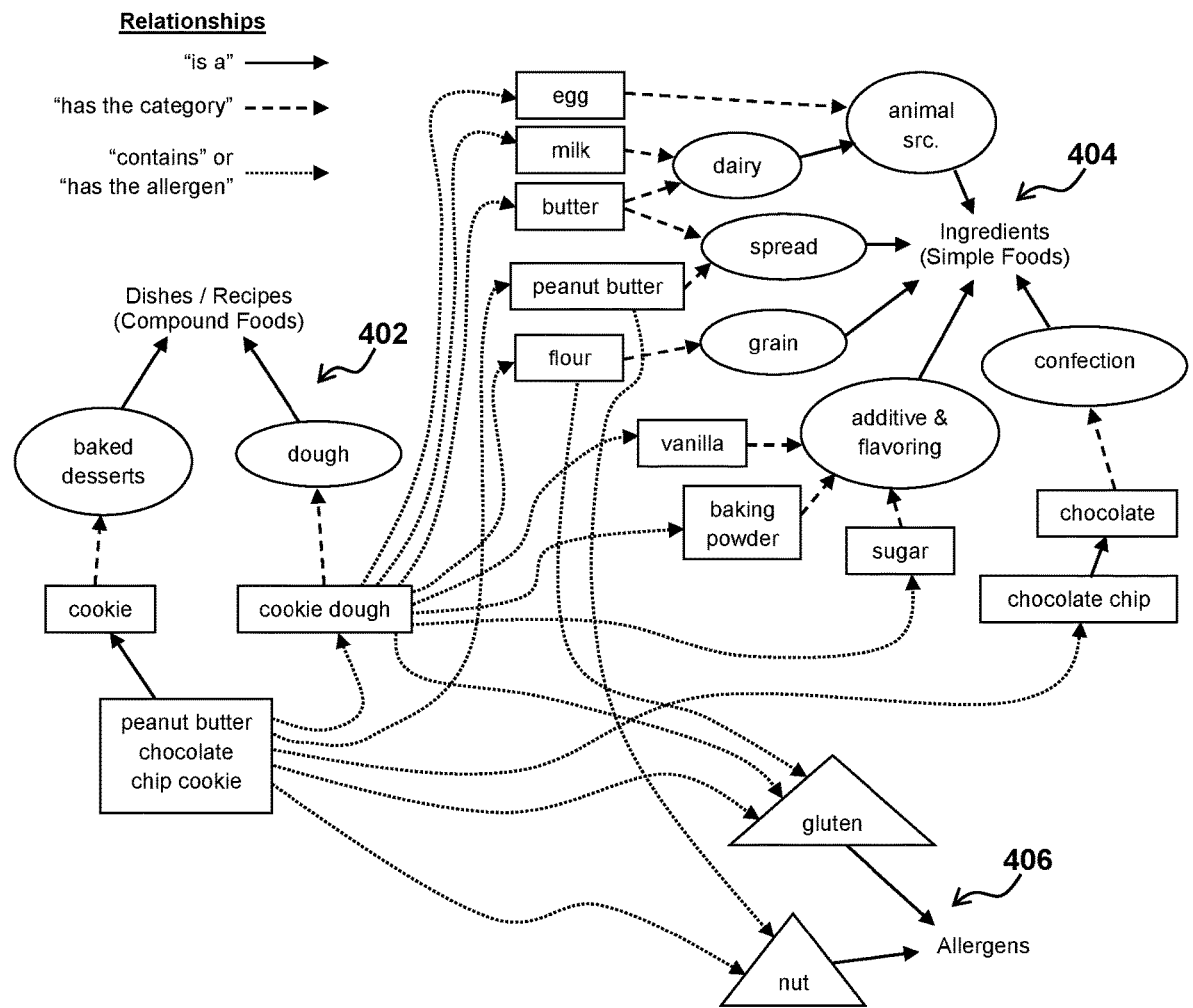
FIG. 4B shows a further exemplary partial food knowledge graph illustrating component relationships that interconnect consumables names of a dish/recipe sub-graph with an ingredient sub-graph and an allergen sub-graph.

FIG. 4B shows a further exemplary partial food knowledge graph illustrating component relationships that interconnect consumables names of a dish/recipe sub-graph 402 with an ingredient sub-graph 404 and an allergen sub-graph 406. Particularly, another exemplary relationship that might be defined in a food knowledge graph is a component relationship ("contains") indicating that a first consumable name contains a second consumable name as a component and/or ingredient. For example, a pizza "contains" cheese, lemonade "contains" a sweetener, a cinnamon roll "contains" cinnamon. One variant of the component relationship that might be defined in a food knowledge graph is an allergen relationship ("has the allergen") indicating that a first consumable name contains a particular allergen. For example, a peanut butter cup "has the allergen" nuts, chocolate milk "has the allergen" diary, and a breadstick "has the allergen" gluten.

The dish/recipe sub-graph 402 and ingredient sub-graph 404 each include a plurality of generic consumable name labels (indicated by a rectangle) and a plurality of categories of consumables (indicated by an oval). As used herein, "dish" and "recipe" (which may also be referred to herein as "compound foods") each refer to consumables and/or consumable names that are decomposed into further subcomponents in the food knowledge graph. In some embodiments, "dish" and "recipe" correspond to different types of consumable records in the database 220, but may be treated as equivalent with respect to the food knowledge graph 230. In other embodiments, separate sub-graphs may be used for "dishes" and "recipes." The ingredient sub-graph 404 is essentially similar to the ingredient sub-graph 400 of FIG. 4A and not described in complete detail. The dish/recipe sub-graph 402 defines ontological relationships between a plurality of dishes and/or recipes, and is essentially analogous to the ingredient sub-graph 400 of FIG. 4A and not described in complete detail. Finally, the allergen sub-graph 406 includes a plurality of allergen labels (indicated by a triangle), and although not shown, may define similar ontological relationships as the aforementioned sub-graphs 400, 402, and 404.

The sub-graphs 402, 404, and 406 include a plurality of component relationships which indicate that a consumable name includes a particular consumable name (indicated by a dotted arrow). Particularly, as illustrated in FIG. 4B, the food knowledge graph defines that a "peanut butter chocolate chip cookie" contains "cookie dough," "peanut butter," and a "chocolate chip." As can be seen dishes and recipes names, a "peanut butter chocolate chip cookie," may contain simple ingredients (e.g. chocolate chips and peanut butter) as well as other compound dishes or recipes (e.g. cookie dough). Particularly, the food knowledge graph defines that the "cookie dough" component itself contains the ingredients "egg," "milk," "butter," "flour," "vanilla," "baking powder," and "sugar."

Furthermore, the sub-graphs 402, 404, and 406 include a plurality of allergen relationships which indicate that a consumable name includes a particular allergen (also indicated by a dotted arrow). Particularly, as illustrated in FIG. 4B, the food knowledge graph defines that a "peanut butter chocolate chip cookie" has the allergens "gluten" and "nut." Additionally, the food knowledge graph defines that "peanut butter" has the allergen "nut" and that "flour" contains "gluten." In this way, the food knowledge graph not only indicates what allergens are contained in a "peanut butter chocolate chip cookie," but also provides sufficient information to eliminate the allergen from a recipe. Particularly, to eliminate the "nut" allergen from a recipe for a "peanut butter chocolate chip cookie," the "peanut butter" ingredient must be omitted or substituted. Similarly, to eliminate the "gluten" allergen from a recipe for a "peanut butter chocolate chip cookie," the "flour" ingredient must be omitted or substituted (such as with a gluten-free flour substitute). As will be discussed in further detail below, the food knowledge graph also provides information regarding dietary substitutes of individual consumable names.

Figure 4C:
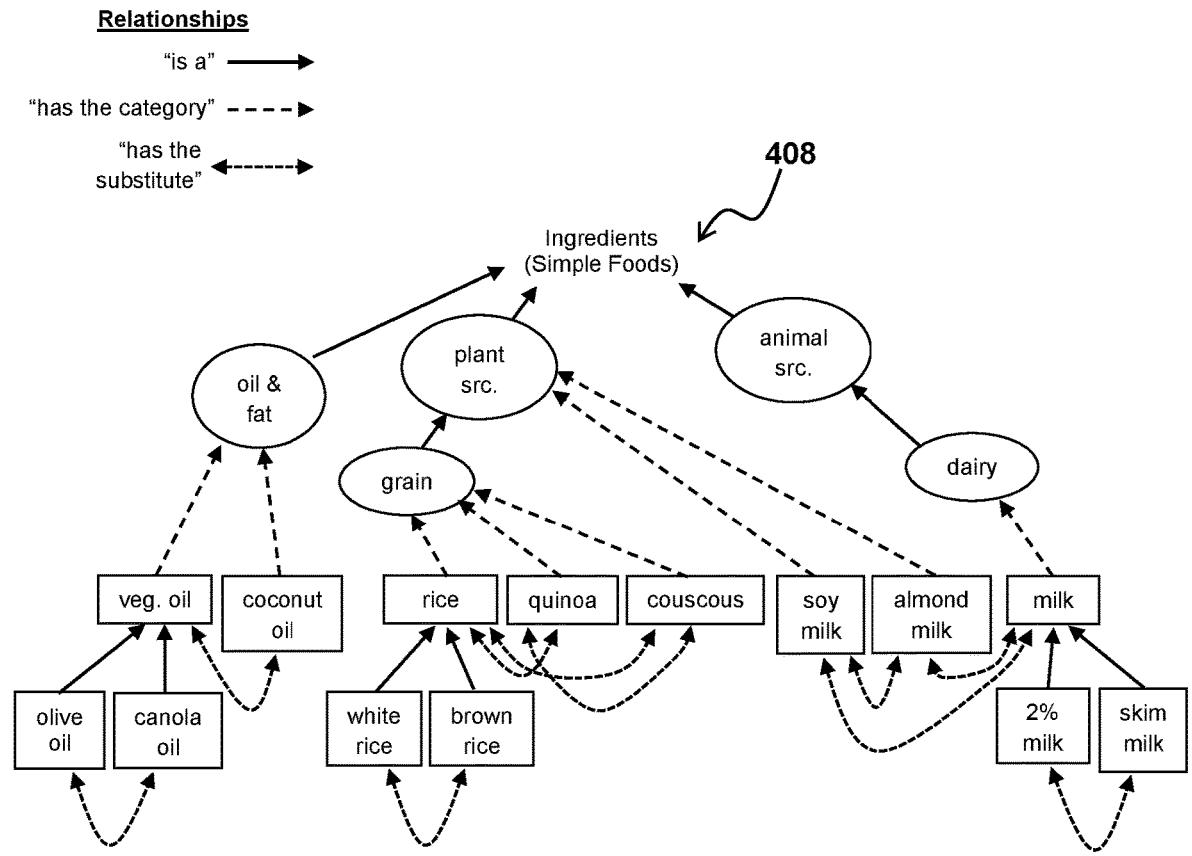
FIG. 4C shows a yet another exemplary partial food knowledge graph illustrating dietary substitute relationships that interconnect consumables names of an ingredient sub-graph.

FIG. 4C shows a yet another exemplary partial food knowledge graph illustrating dietary substitute relationships that interconnect consumables names of an ingredient sub-graph 408. Particularly, another exemplary relationship that might be defined in a food knowledge graph is a substitute relationship ("has the substitute") indicating that a first consumable name has as a dietary substitute a second consumable name. For example, ketchup "has the substitute" mustard, cream "has the substitute" milk, and sugar "has the substitute" stevia extract. In some embodiments, the food knowledge graph may define multiple types of substitutions. In one embodiment, the food knowledge graph separately defines substitutes that are sufficiently similar to substitute in a recipe (e.g., butter "has the substitute" margarine). In some embodiments, the food knowledge graph separately defines substitutes that are similar in flavor (e.g., grape jelly "has the substitute" strawberry jelly). In some embodiments, the food knowledge graph separately defines substitutes that are sufficiently similar in function (e.g., ketchup "has the substitute" mayonnaise).

The ingredient sub-graph 408 includes a plurality of generic consumable name labels (indicated by a rectangle) and a plurality of categories of consumables (indicated by an oval). The ingredient sub-graph 408 is essentially similar to the ingredient sub-graph 400 of FIG. 4A and not described in complete detail. The ingredient sub-graph 408 includes a plurality of dietary substitute relationships which indicate that a consumable name has as a dietary substitute another consumable name (indicated by a double sided dashed arrow). Particularly, as illustrated in FIG. 4C, the food knowledge graph defines that vegetable oil "has the substitute" coconut oil, and visa versa. Additionally, the food knowledge graph defines that olive oil "has the substitute" canola oil, and visa versa. Furthermore, since olive oil and canola oil are subclasses of vegetable oil, it is known that both olive oil and canola oil also "have the substitute" coconut oil. Similarly, the food knowledge graph defines that rice, quinoa, and couscous are each substitutes for one another. Additionally, the food knowledge graph defines that white rice "has the substitute" brown rice, and visa versa. Furthermore, since white rice and brown rice are subclasses of rice, it is known that both white rice and brown rice also "have the substitutes" quinoa and couscous, and visa versa.

Finally, the food knowledge graph defines that milk, soy milk, and almond milk are each substitutes for one another. Additionally, the food knowledge graph defines that 2% milk "has the substitute" skim milk, and visa versa. Furthermore, since 2% milk and skim milk are subclasses of milk, it is known that both 2% milk and skim milk also "have the substitutes" soy milk and almond milk, and visa versa.

In the embodiment shown, when a particular consumable name has as a substitute a class of consumables and its respective subclasses of consumables, it is only directly related to the broader class of consumables. For example, coconut oil only has a direct dietary substitute relationship with vegetable oil, and it is simply implied that all of the subclasses of vegetable oil (i.e. olive oil and canola oil, as shown) are also substitutes. However, in other embodiments, a particular consumable name might also have a directly defined dietary substitute relationship with a broader class of consumables and every subclass thereof.

Figure 4D:
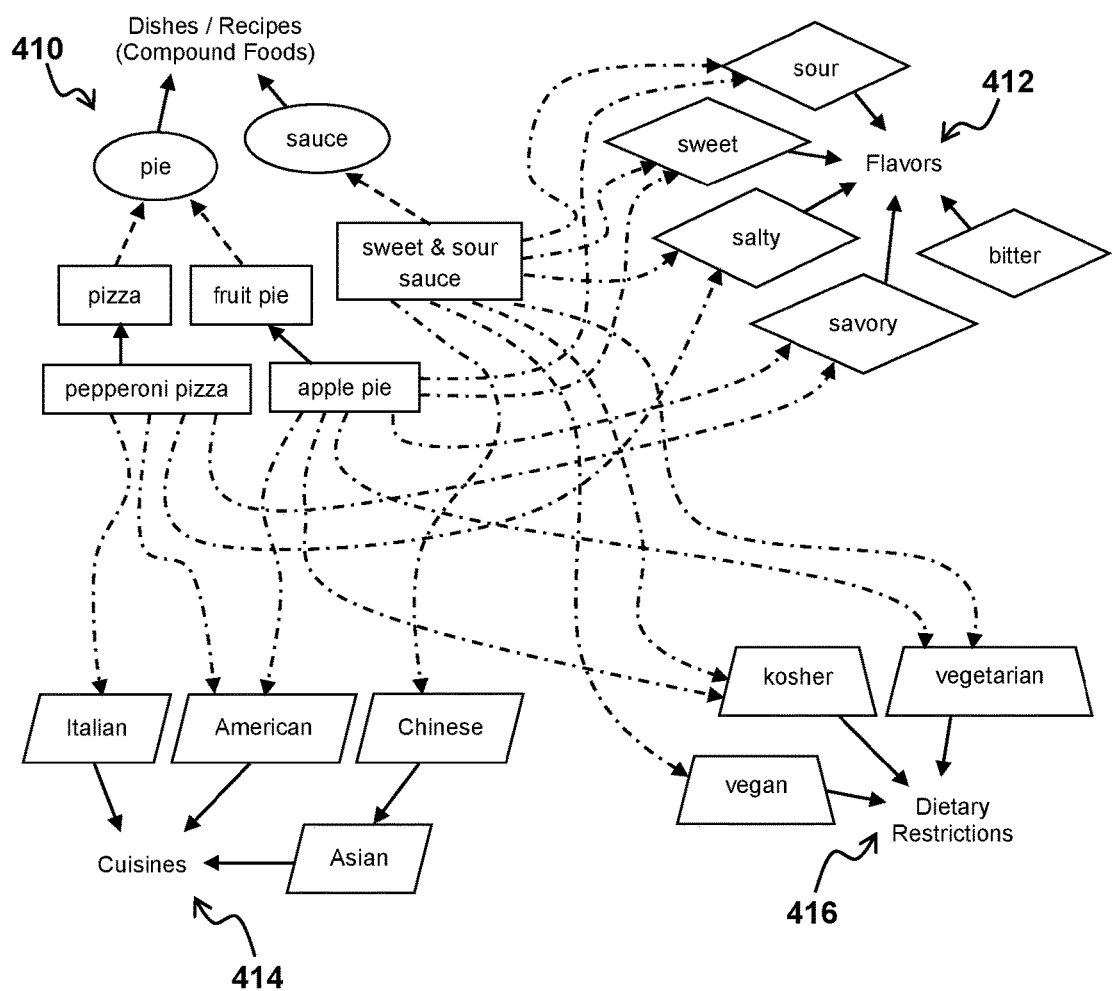
FIG. 4D shows a yet another exemplary partial food knowledge graph illustrating attribute relationships that interconnect consumables names of a dish/recipe sub-graph with a flavor sub-graph, a cuisine sub-graph, and a dietary restriction sub-graph.

FIG. 4D shows a yet another exemplary partial food knowledge graph illustrating attribute relationships that interconnect consumables names of a dish/recipe sub-graph 410 with a flavor sub-graph 412, a cuisine sub-graph 414, and a dietary restriction sub-graph 416. Particularly, one exemplary attribute relationship that might be defined in a food knowledge graph is a flavor relationship ("has the flavor") indicating that a first consumable name has as a particular flavor. For example, a pretzel "has the flavor" salty, cake "has the flavor" sweet, and a lemon "has the flavor" sour. Another exemplary attribute relationship that might be defined in a food knowledge graph is a cuisine relationship ("is from the cuisine") indicating that a first consumable name is from a particular cuisine. For example, spaghetti "is from the cuisine" Italian, curry chicken "is from the cuisine" Indian, and spring roll "is from the cuisine" Chinese. Yet another exemplary attribute relationship that might be defined in a food knowledge graph is a dietary restriction relationship ("is compliant with") indicating that a first consumable name is compliant with a particular dietary restriction. For example, a ceasar salad "is compliant with" vegetarian, tofu "is compliant with" vegan, and an all-beef hot dog "is compliant with" kosher.

The dish/recipe sub-graph 410 includes a plurality of generic consumable name labels (indicated by a rectangle) and a plurality of categories of consumables (indicated by an oval). The dish/recipe sub-graph 410 is essentially similar to the ingredient sub-graph 400 of FIG. 4A and not described in complete detail. The flavor sub-graph 412 includes a plurality of flavors (indicated by a rhombus). As shown, the flavor sub-graph 412 only includes the fundamental flavors. However, in some embodiments, the flavor sub-graph 412 may also include compound flavors (e.g., buttery, tangy, fruity) with ontological relationships defined therebetween. Additionally, the cuisine sub-graph 414 includes a plurality of cuisines (indicated by a parallelogram) and ontological relationships defined therebetween. Finally, the cuisine sub-graph 414 includes a plurality of dietary restrictions (indicated by a trapezoid) and, although none are shown, may also include ontological relationships defined therebetween.

The sub-graphs 410 and 412 are connected by a plurality of flavor relationships which indicate that a consumable name has a particular flavor (indicated by a dash-dotted arrow). Particularly, as illustrated in FIG. 4D, the food knowledge graph defines that a pepperoni pizza "has the flavors" savory and salty. Similarly, the food knowledge graph defines that an "apple pie "has the flavors" sweet, sour, and savory. Finally, the food knowledge graph defines that sweet & sour sauce "has the flavors" sweet, sour, and salty.

The sub-graphs 410 and 414 are connected by a plurality of cuisine relationships which indicate that a consumable name is from a particular cuisine (also indicated by a dash-dotted arrow). Particularly, as illustrated in FIG. 4D, the food knowledge graph defines that a pepperoni pizza "is from the cuisines" Italian and American. Similarly, the food knowledge graph defines that an "apple pie "is from the cuisine" American. Finally, the food knowledge graph defines that sweet & sour sauce "is from the cuisine" Chinese.

The sub-graphs 410 and 416 are connected by a plurality of dietary restriction relationships which indicate that a consumable name is compliant with a particular dietary restriction (also indicated by a dash-dotted arrow). Particularly, as illustrated in FIG. 4D, the food knowledge graph defines that an "apple pie "is compliant with" kosher and vegetarian dietary restrictions, but not a vegan dietary restriction. Similarly, the food knowledge graph defines that sweet & sour sauce "is compliant with" kosher, vegan, and vegetarian dietary restrictions. As can be see, the food knowledge graph does not define that a pepperoni pizza "is compliant with" any of the illustrated dietary restrictions.

Figure 4E:
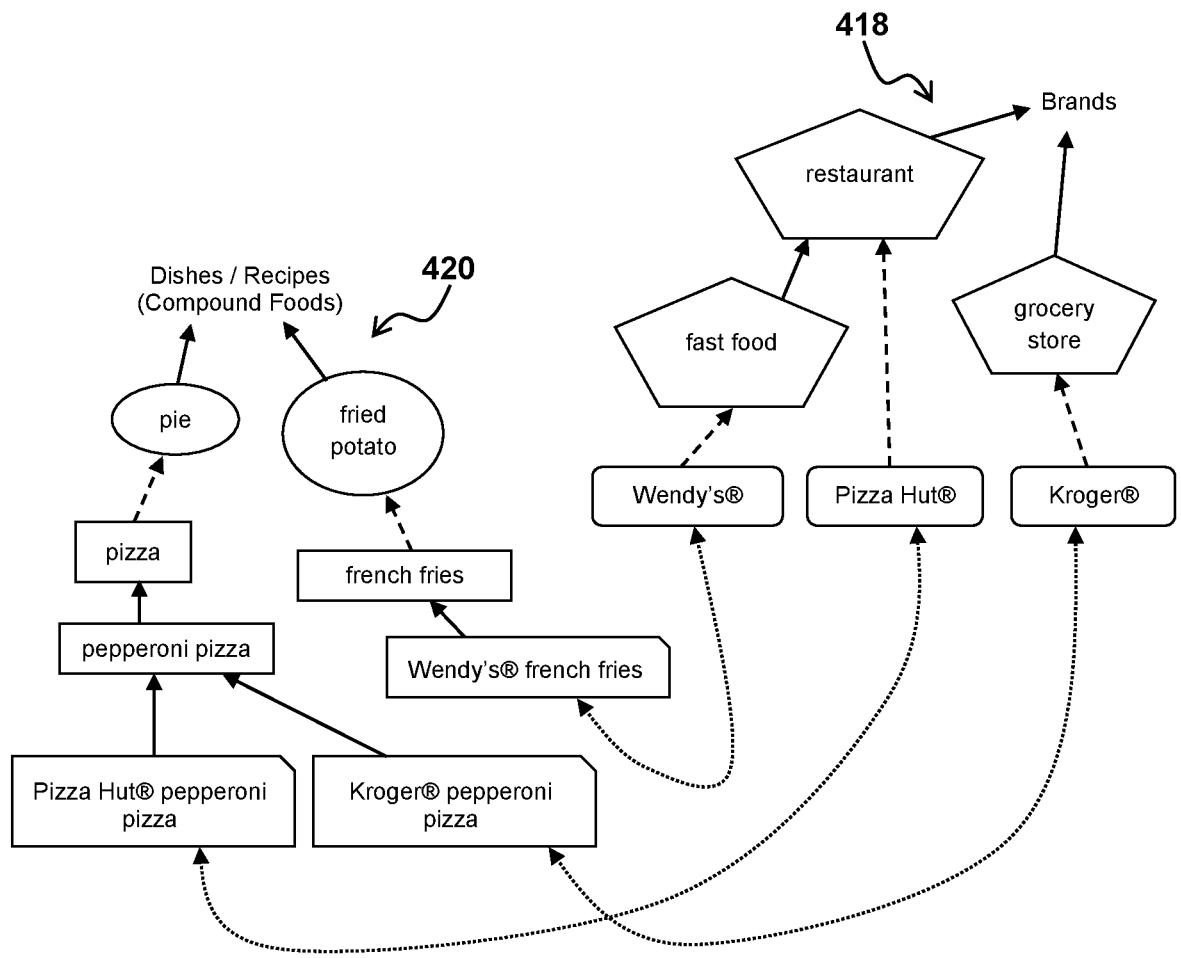
FIG. 4E shows a yet another exemplary partial food knowledge graph illustrating ontological relationships between brand names of a brand name sub-graph and brand relationships between branded consumable names of a dish/recipe sub-graph and brand names of the brand name sub-graph.

FIG. 4E shows a yet another exemplary partial food knowledge graph illustrating ontological relationships between brand names of a brand name sub-graph 418 and brand relationships between branded consumable names of a dish/recipe sub-graph 420 and brand names of the brand name sub-graph 418. Particularly, in some embodiments, the descriptive labels may include popular branded consumable names (e.g., Kraft Easy Mac®, McDonald's McNuggets®), in addition to generic consumable names. In such embodiments, another exemplary relationship that might be defined in a food knowledge graph is a brand relationship ("has the brand" or "sells") indicating that a branded consumable name has a particular brand name or that a particular brand name sells a particular branded consumable name. For example, Mountain Dew® "has the brand" Pepsi® and McDonald's® "sells" Big Mac®.

The brand name sub-graph 418 includes a plurality of brand names (indicated by a rounded rectangle) and a plurality of categories of brand names (indicated by a pentagon). The dish/recipe sub-graph 420 includes a plurality of generic consumable name labels (indicated by a rectangle), branded consumable name labels (indicated by a rectangle having a beveled corner) and a plurality of categories of consumables (indicated by an oval). The dish/recipe sub-graph 420 is essentially similar to the ingredient sub-graph 400 of FIG. 4A and not described in complete detail.

The sub-graphs 418 and 420 are connected by a plurality of brand relationships which indicate that a branded consumable name has a particular brand name or that a particular brand name sells a particular branded consumable name (indicated by a double-sided dotted arrow). Particularly, as illustrated in FIG. 4E, the food knowledge graph defines that Pizza Hut® Pepperoni Pizza "has the brand" Pizza Hut® and, similarly, that Pizza Hut® "sells" Pizza Hut® Pepperoni Pizza. Additionally, the food knowledge graph defines that Kroger® Pepperoni Pizza "has the brand" Kroger® and, similarly, that Kroger® "sells" Kroger® Pepperoni Pizza. Finally, the food knowledge graph defines that Wendy's® french fries "has the brand" Wendy's® and, similarly, that Wendy's® "sells" Wendy's® french fries.

Furthermore, the ingredient sub-graph 418 includes a plurality of ontological relationships which relate the brand names and the categories of brand names in a manner similar to the ingredient and dish/recipe sub-graphs discussed above. Particularly, as illustrated in FIG. 4E, the food knowledge graph defines that Wendy's® "has the category" fast food, which itself "is a" subclass of restaurant. Similarly, the food knowledge graph defines that Pizza Hut® "has the category" restaurant. Finally, the food knowledge graph defines that Kroger® "has the category" grocery store.

Methods of Using the Food Knowledge Graph

Various methods and processes for operating a health tracking system are described below. In the description of the methods, statements that a method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 204 of the system server 200 and/or the processor 308 of the smartphone 110A above may be such a controller or processor. Alternatively, the controller may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Figure 5:
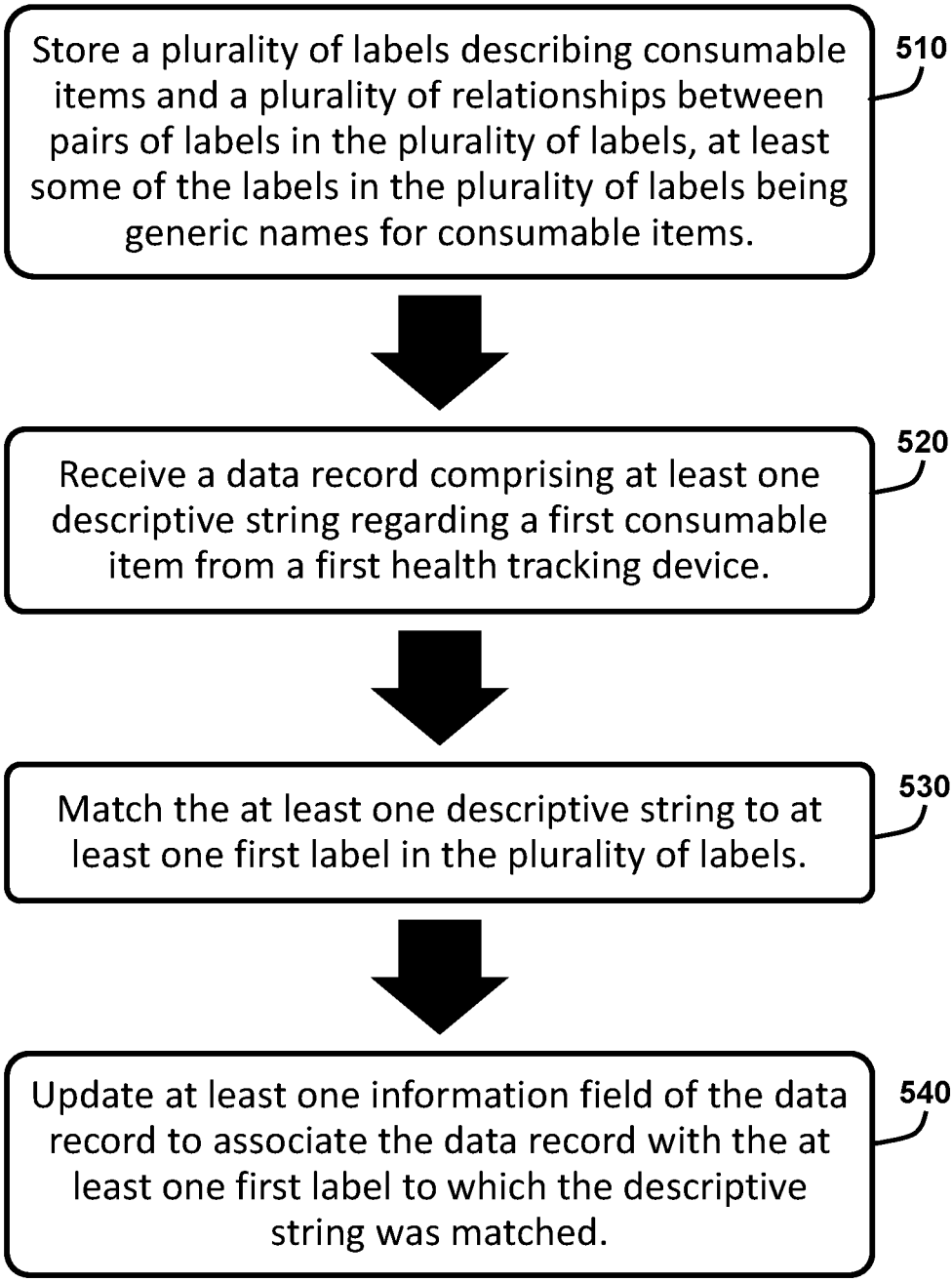
FIG. 5 shows a method of operating the health tracking system to generate supplemental information for consumable records using the food knowledge graph.

FIG. 5 shows a method 500 of operating the health tracking system 100 to generate supplemental information for consumable records using the food knowledge graph 230. The method 500 improves the functioning of the system server 200 by enabling the processor circuitry/logic 204 to utilize the structured knowledge defined by the food knowledge graph 230 to provided additional information and/or metadata which is stored in or referenced by consumable records, in addition to the user-generated information of the consumable records. Particularly, in some embodiments, many, if not all, of consumable records 224 are created by users of the health tracking system 100 and/or have fields that are editable by users, without the need for special authorization or privileges. However, the user-generated information in the consumable records 224 is often limited to nothing more than a basic user-generated text description and basic nutritional content information. The method 500 supplements this basic user-generated information by labeling the consumable records 224 with additional information such as a standardized generic consumable name, a consumable category, a standardized brand name, a brand name category, dietary substitutes, included ingredients, included allergens, flavors, a type of cuisine, dietary restriction compliance, and other miscellaneous useful descriptive labels.

The method 500 begins with a step of storing a plurality of labels describing consumable items and a plurality of relationships between pairs of labels in the plurality of labels, at least some of the labels in the plurality of labels being generic names for consumable items (block 510). Particularly, with respect to the embodiments disclosed in detail herein, the processor circuitry/logic 204 of the system server 200 is configured to operate the database 220 to store the food knowledge graph 230. The food knowledge graph 230 comprises a plurality of descriptive labels describing consumable items and a plurality of relationships between pairs or groups of labels in the plurality of descriptive labels. In one embodiment, the descriptive labels of the food knowledge graph 230 at least include generic consumable names, but may include any other type of descriptive label discussed above with respect to FIGS. 4A-4E or any other useful descriptive labels not discussed above. Furthermore, the plurality of relationships of the food knowledge graph 230 may include any of the relationship types discussed above with respect to FIGS. 4A-4E, as well as any other useful relationship type not discussed above. In some embodiments, the processor circuitry/logic 204 is configured to operate the database 220 to store the food knowledge graph 230 in the form of one or more lists or tables that define a data tree or data web in which the descriptive labels comprise the nodes of the tree or web and the relationships comprise the connections between the nodes of the tree or web (for example, as illustrated in FIGS. 4A-4E). In one embodiment, the processor circuitry/logic 204 is configured to operate the database 220 to store the food knowledge graph 230 in the form of a reduced number of self-referential lists or tables, possible a single self-referential list or table, that define all of the labels and relationships that form the data tree or data web. In some embodiments, the processor circuitry/logic 204 is configured to operate the database 220 to store the labels and/or relationships as a list or table of triplets formed as, for example, [label_ID1, relationship_type, label_ID2] where label_ID1 is a first descriptive label or reference thereto, label_ID2 is a second descriptive label or reference thereto, and relationship_type indicates the nature of the relationship. However, the food knowledge graph can take any other suitable form.

The method 500 continues with a step of receiving a data record comprising at least one descriptive string regarding a first consumable item from a first health tracking device (block 520). Particularly, the processor circuitry/logic 204 is configured to operate the network communications module 212 to receive a consumable record from a health tracking device 110, such as the smartphone 110A. Alternatively, the processor circuitry/logic 204 is configured to read from the database 220, a consumable record which was previously received from a health tracking device 110. The received consumable record includes at least one descriptive string that describes a consumable item, which was entered by the user who created the consumable record. In some embodiments, the received consumable record includes both an item description string that describes the consumable item and a brand description string that describes a brand of the consumable item, which were entered by the user who created the consumable record. In the case that the received consumable record is a recipe, the consumable record may further include one or more ingredient description strings. In some embodiments, the received consumable record further includes nutritional content information, which was entered by the user who created the consumable record.

Figure 6A:
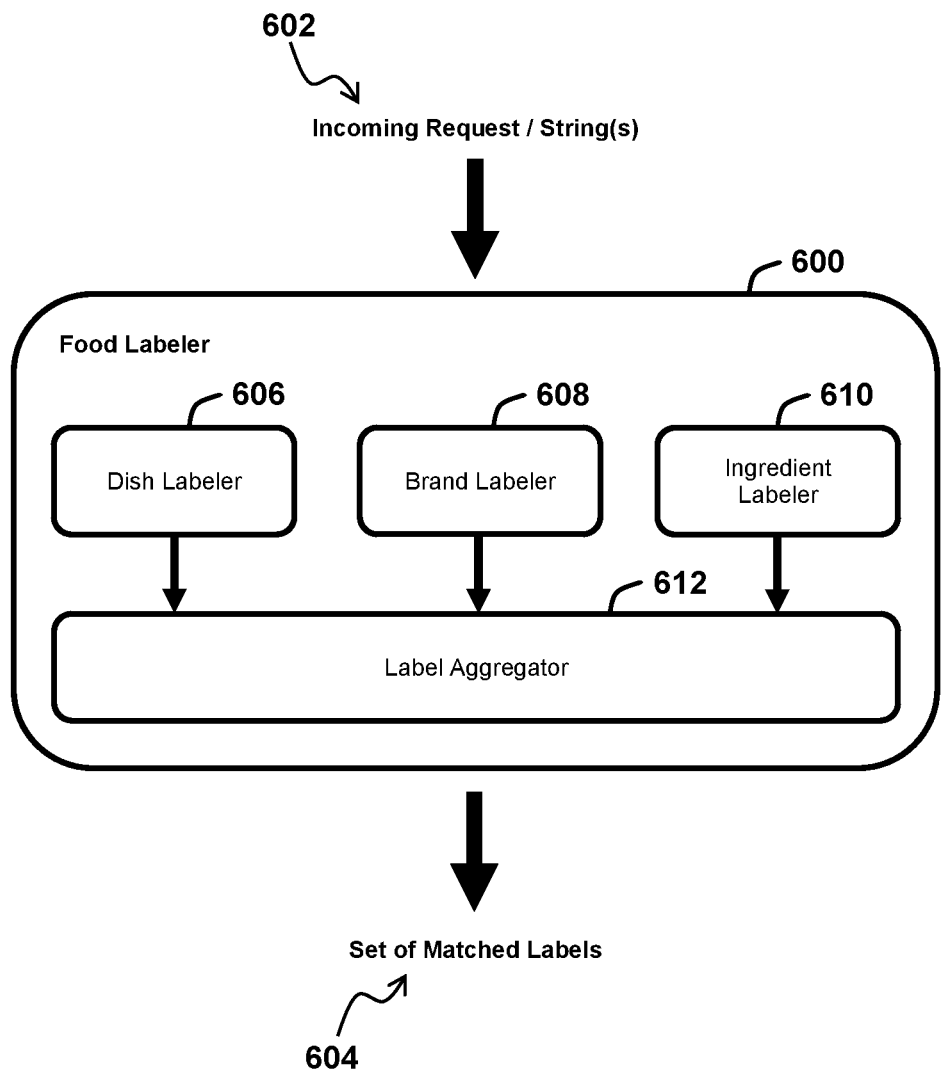
FIG. 6A shows a food labeler of the health tracking application.

The method 500 continues with a step of matching the at least one descriptive string to at least one first label in the plurality of labels (block 530). Particularly, the processor circuitry/logic 204 is configured to execute a food labeling process of the health tracking application 218 to match the at least one descriptive string with one or more descriptive labels of the food knowledge graph 230. FIG. 6A shows a food labeler 600 of the health tracking application 218 of the system server. The food labeler 600 is configured to, when executed by the processor circuitry/logic 204, match at least one descriptive string 602 with one or more descriptive labels of the food knowledge graph 230 and output a set of matched labels 604. In one embodiment, the food labeler 600 is configured to, when executed by the processor circuitry/logic 204, compare the text of a respective descriptive string with the labels and match the respective descriptive string to the most similar label of the food knowledge graph 230 or labels of the food knowledge graph 230 having a threshold level of similarity. In some embodiments, rather than using a rules-based text comparison, the food labeler 600 is configured to, when executed by the processor circuitry/logic 204, instead use a machine learning model to match the descriptive strings of the received consumable record to labels of the food knowledge graph 230.

In one embodiment, the food labeler 600 includes three separate labelers, a dish labeler 606, a brand labeler 608, and an ingredient labeler 610. The dish labeler 606 is configured to, when executed by the processor circuitry/logic 204, match an item description string of the received consumable record with at least one label of the food knowledge graph 230. Particularly, in one embodiment, the dish labeler 606 is configured to match the item description string of the received consumable record with a most similar generic consumable name label of the food knowledge graph 230. Similarly, the brand labeler 608 is configured to, when executed by the processor circuitry/logic 204, match a brand description string of the received consumable record with at least one label of the food knowledge graph 230. Particularly, in one embodiment, the brand labeler 608 is configured to match the brand description string of the received consumable record with a most similar brand name label of the food knowledge graph 230. Finally, in the case that the received consumable record is a recipe, the ingredient labeler 610 is configured to, when executed by the processor circuitry/logic 204, match one or more ingredient description strings of the received consumable record with at least one label of the food knowledge graph 230. Particularly, in one embodiment, the brand labeler 608 is configured to match each ingredient in the one or more ingredient description strings of the received consumable record with a most similar generic consumable name of the food knowledge graph 230. In one embodiment, the food labeler 600 includes a label aggregator configured to aggregate or otherwise process the matched labels to provide the set of matched labels 604.

Figure 6B:
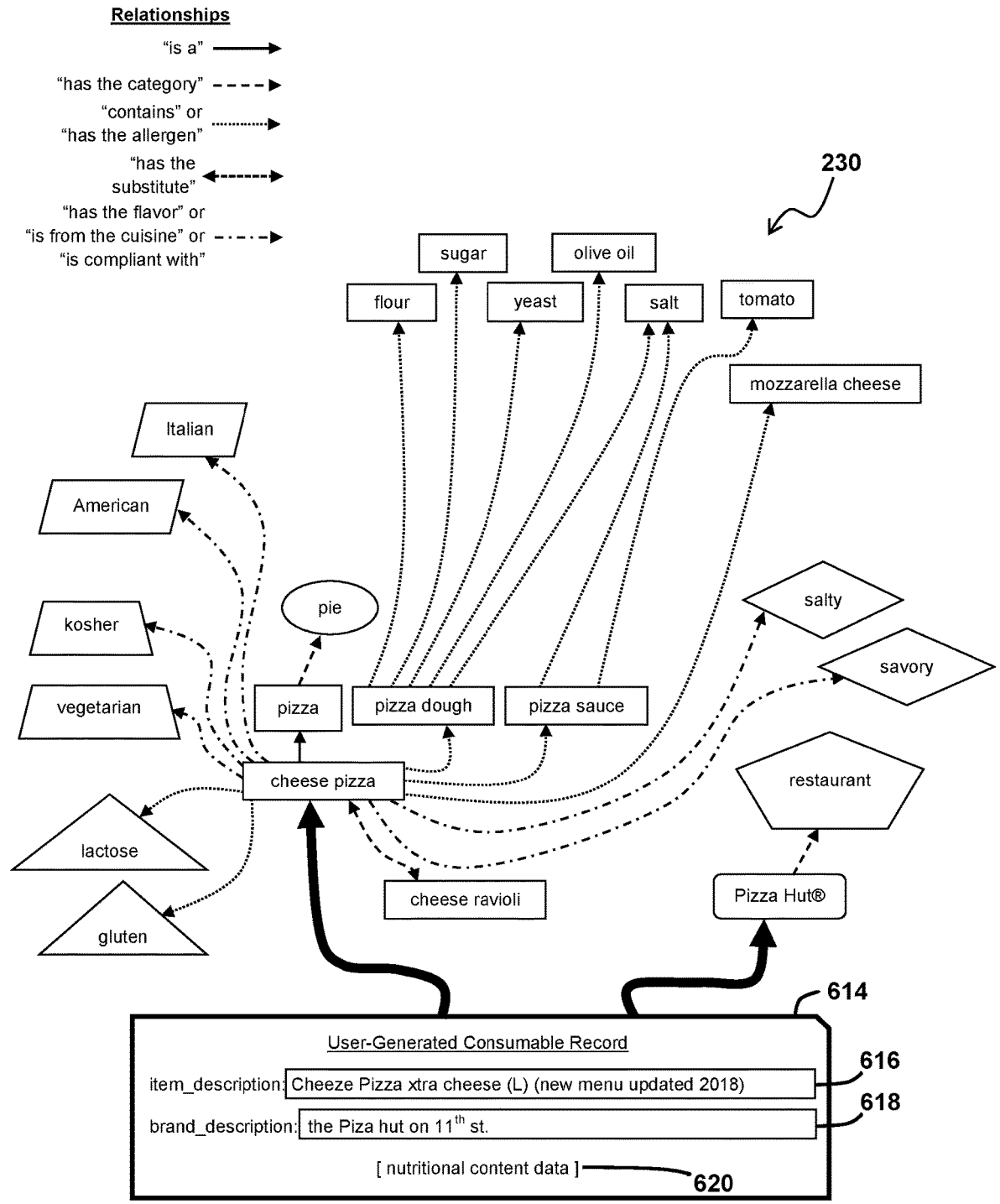
FIG. 6B shows an exemplary matching of a consumable record to the food knowledge graph.

FIG. 6B shows an exemplary process for matching a consumable record 614 to a set of labels of the food knowledge graph 230 (only partially shown). Particularly, the consumable record 614 is received by the processor circuitry/logic 204 and includes an item description field 616, a brand description field 618, and nutritional content data 620. The item description field includes the item description string "Cheeze Pizza xtra cheese (L) (new menu updated 2018)" and the brand description field includes the brand description string "the Piza hut on 11$^{th}$ st." As can be seen, the item description string and the brand description string include typographical errors (e.g., "Cheeze" and "Piza"), non-standard acronyms (e.g., "xtra"), in-consistent capitalization, and extraneous information (e.g. "new menu updated 2018" and "on 11$^{th}$ st.").

In the example shown, the dish labeler 606 of the food labeler 600 has directly matched the item description string (i.e., "Cheeze Pizza xtra cheese (L) (new menu updated 2018)") to the label "cheese pizza," which is the most similar generic consumable name label. Similarly, the brand labeler 608 of the food labeler 600 has directly matched the brand description string (i.e., "the Piza hut on 11$^{th}$ st.") to the label "Pizza Hut®," which is the most similar brand name label. The matched generic consumable name label (i.e., "cheese pizza") and matched brand name label (i.e., "Pizza Hut®") can be considered the direct matches of the descriptive strings of received consumable record 614. In contrast with the item description and brand description strings, the matched generic consumable name and brand name labels are standardized and free of errors, making them more useful for performing database operations, such as search.

In some embodiments, the food labeler 600 is further configured to identify additional labels of the food knowledge graph 230 that are related to the directly matched labels, as defined by the food knowledge graph 230. In the example shown, the dish labeler 606 identifies that "cheese pizza" is a subclass of "pizza" based on the ontological relationships defined by the food knowledge graph 230. Accordingly, the dish labeler 606 further matches the "pizza" generic consumable name label to the item description string of consumable record 614. Similarly, the dish labeler 606 identifies that "cheese pizza" and "pizza" are in the "pie" category of consumables based on the ontological relationships defined by the food knowledge graph 230. Accordingly, the dish labeler 606 further matches the "pie" category of consumables label to the item description string of consumable record 614. Furthermore, the dish labeler 606 identifies that "cheese pizza" has the substitute "cheese ravioli" based on the substitute relationships defined by the food knowledge graph 230. Accordingly, the dish labeler 606 further matches the "cheese ravioli" generic consumable name label to the item description string of consumable record 614.

The dish labeler 606 also identifies that "cheese pizza" has the ingredients "mozzarella cheese," "pizza sauce," and "pizza dough" based on the component relationships defined by the food knowledge graph 230. Similarly, the dish labeler 606 identifies that "pizza sauce" has the ingredients "tomato" and "salt" and that "pizza dough" has the ingredients "flour," "sugar," "yeast," "olive oil," and "salt" based on the component relationships defined by the food knowledge graph 230. Accordingly, the dish labeler 606 further matches the "mozzarella cheese," "pizza sauce," "pizza dough," "tomato," "flour," "sugar," "yeast," "olive oil," and "salt" generic consumable name labels to the item description string of consumable record 614.

The dish labeler 606 further identifies that "cheese pizza" contains the allergens "lactose" and "gluten" based on the allergen relationships defined by the food knowledge graph 230. Accordingly, the dish labeler 606 further matches the "lactose" and "gluten" allergen labels to the item description string of consumable record 614. Similarly, the dish labeler 606 identifies that "cheese pizza" is compliant with the "kosher" and "vegetarian" dietary restrictions based on the dietary restriction relationships defined by the food knowledge graph 230. Accordingly, the dish labeler 606 further matches the "kosher" and "vegetarian" dietary restriction labels to the item description string of consumable record 614. Furthermore, the dish labeler 606 identifies that "cheese pizza" has flavors "savory" and "salty" based on the flavor relationships defined by the food knowledge graph 230. Accordingly, the dish labeler 606 further matches the "savory" and "salty" flavor labels to the item description string of consumable record 614. Finally, the dish labeler 606 identifies that "cheese pizza" is from the cuisines "Italian" and "American" based on the cuisine relationships defined by the food knowledge graph 230. Accordingly, the dish labeler 606 further matches the "Italian" and "American" cuisine labels to the item description string of consumable record 614.

Also in the example shown, the brand labeler 608 identifies that "Pizza Hut®" is in the "restaurant" category of brand names based on the ontological relationships defined by the food knowledge graph 230. Accordingly, the brand labeler 608 further matches the "restaurant" category of brand names label to the brand description string of consumable record 614.

The method 500 continues with a step of at least one information field of the data record to associate the data record with the at least one first label to which the descriptive string was matched (block 540). Particularly, the processor circuitry/logic 204 is configured to update and/or modify at least one information field of the received consumable record to associate the consumable record with the set of matched labels 604 provided by the labeler 600. In one embodiment, the consumable record simply includes a labels field and the processor circuitry/logic 204 is configured to add the matched labels or references thereto into the labels field. However, in some embodiments, the consumable record includes several fields corresponding to the various types of labels and the processor circuitry/logic 204 is configured to add the matched labels or references thereto into the appropriate corresponding fields of the consumable record.

Figure 6C:
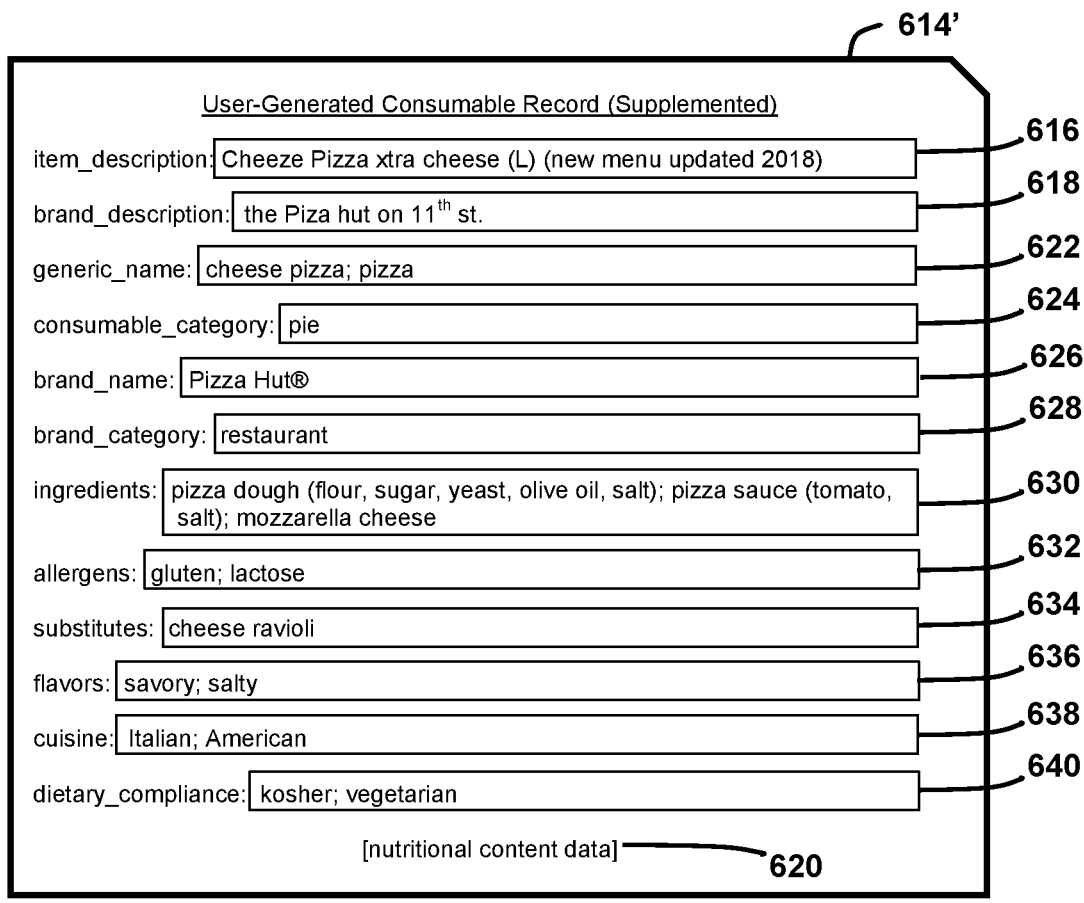
FIG. 6C shows an exemplary updated consumable record which has been updated based on the labels to which the consumable record of FIG. 6B was matched.

FIG. 6C shows an exemplary supplemented consumable record 614' which has been updated based on the labels to which the consumable record 614 of FIG. 6B was matched. Particularly, a generic_name field 622 of the supplemented consumable record 614' is updated to associate the record with the "cheese pizza" and "pizza" generic consumable name labels. Similarly, a consumable category 624 field of the supplemented consumable record 614' is updated to associate the record with the "pie" category of consumables label. A brand_name field 626 of the supplemented consumable record 614' is updated to associate the record with the "Pizza Hut®" brand name label. A brand_category field 628 of the supplemented consumable record 614' is updated to associate the record with the "restaurant" category of brand names label. An ingredients field 630 of the supplemented consumable record 614' is updated to associate the record with the "mozzarella cheese," "pizza sauce," "pizza dough," "tomato," "flour," "sugar," "yeast," "olive oil," and "salt" generic consumable name labels. An allergen field 632 of the supplemented consumable record 614' is updated to associate the record with the "lactose" and "gluten" allergen labels. A substitutes field 634 of the supplemented consumable record 614' is updated to associate the record with the "cheese ravioli" generic consumable name label. A flavors field 636 of the supplemented consumable record 614' is updated to associate the record with the "savory" and "salty" flavor labels. A cuisine field 638 of the supplemented consumable record 614' is updated to associate the record with the "Italian" and "American" cuisine labels. Finally, a dietary compliance field 640 of the supplemented consumable record 614' is updated to associate the record with the "kosher" and "vegetarian" dietary restriction labels.

As discussed in more detail below, in many embodiments, the processor circuitry/logic 204 of the system server 200 receives some kind of request for data consumable from a health tracking device 110, such as search request or a recommendations request. The processor circuitry/logic 204 is configured to matching the request for consumable records to one or more relevant descriptive labels of the food knowledge graph 230. Based on the matched descriptive labels, the processor circuitry/logic 204 is configured to provide one or more consumable records to the health tracking device 110 that are associated with the matched descriptive labels.

Figure 7:
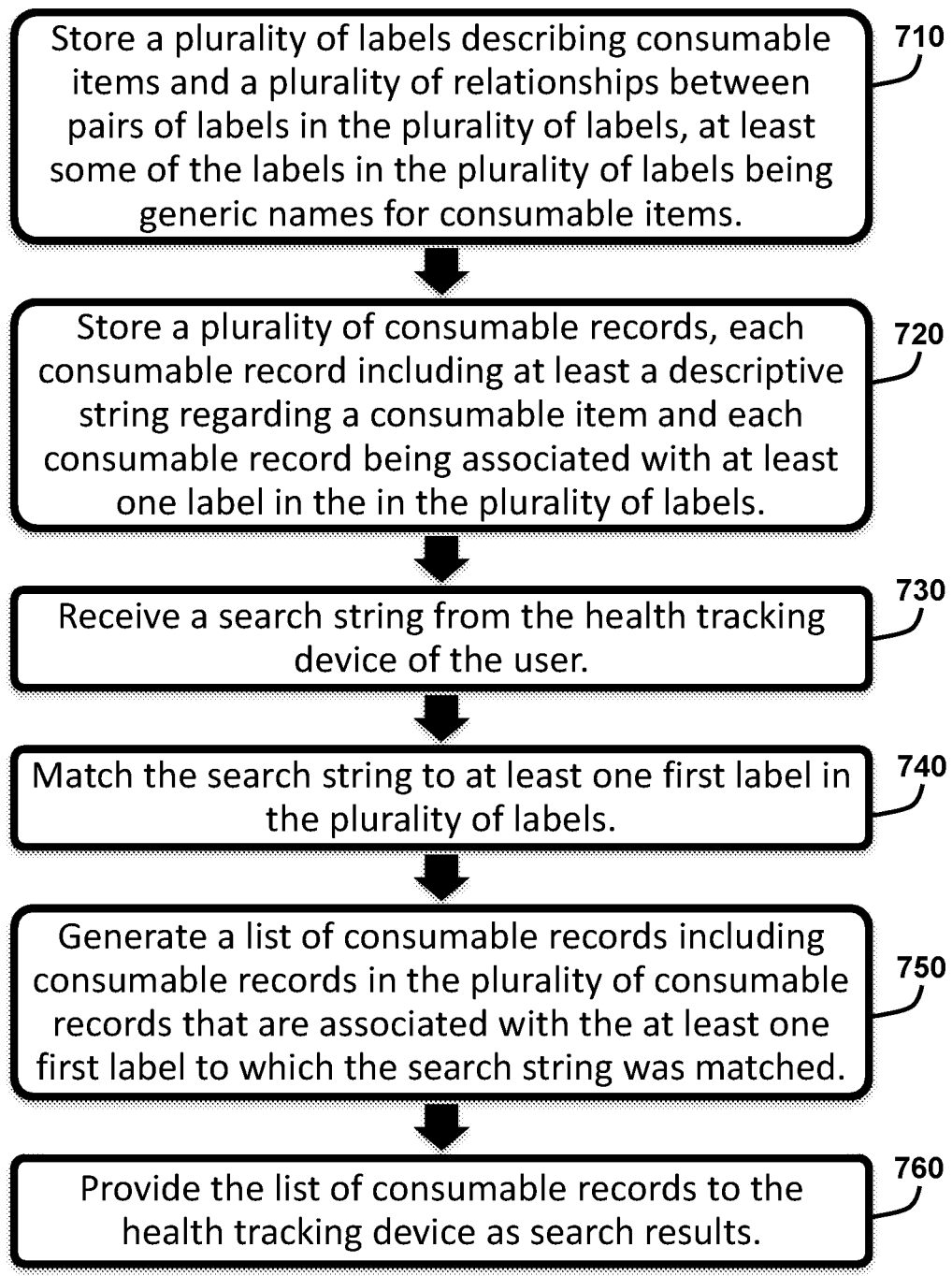
FIG. 7 shows a method of operating the health tracking system to provide improved search results using the food knowledge graph.

FIG. 7 shows a method 700 of operating the health tracking system 100 to provide improved search results using the food knowledge graph 230. Particularly, the method 700 utilizes the food knowledge graph 230, the additional information and/or metadata generated therewith, to provide search results based on a search string. The method 700 improves the functioning of the system server 200 by enabling the processor circuitry/logic 204 to generate a list of consumable records based on search string that are more relevant than would be provided based only on conventional text-comparison based searching.

Figure 8A:
FIG. 8A shows an exemplary graphical user interface including results of a search was performed only on the basis user-generated descriptions of the consumable records.

FIG. 8A shows an exemplary graphical user interface displayed on the smartphone 110A, in which a search of the consumable records 224 was performed in a conventional manner only on the basis of the user-generated item description and brand description strings of the consumable records. As can be seen, a user has entered the search string "mac n cheese" into a search window 810 of the graphical user interface. However, the search results 820 displayed on the graphical user interface include several prominently ranked consumable records that are duplicative, of low relevance, and of low quality. For example, in the search results 820, the second result having the item description "Generic," the third result having the item description "Homemade Macaroni and Cheese," and the fifth result having the item description "Mac N' Cheese," can be considered mostly duplicative of one another because they are all generic records. Additionally, the sixth result having the item description "Macaroni and Cheese Pie," and the eighth result having the item description "Ham and Cheese Macaroni" are likely of low relevance to the search string "mac n cheese" because a user actually searching for these records would have likely used a more specific search term including the word "pie" or "ham," respectively. Furthermore, the second result can be considered low quality because the item and brand descriptions are reversed (i.e. the item description is "Generic" and brand description is "Macaroni and Cheese"). Similarly, the fourth result can also be considered low quality because it is ambiguous what the consumable item actually is (i.e., the item description is "Cheese" and the brand description is "Macaroni").

Returning to FIG. 7, the method 700 uses the food knowledge graph 230 to eliminate many of the issues with a conventional text-comparison based search. Particularly, the method 700 begins with a step of storing a plurality of labels describing consumable items and a plurality of relationships between pairs of labels in the plurality of labels, at least some of the labels in the plurality of labels being generic names for consumable items (block 710). Particularly, with respect to the embodiments disclosed in detail herein, the processor circuitry/logic 204 of the system server 200 is configured to operate the database 220 to store the food knowledge graph 230. The food knowledge graph 230 comprises a plurality of descriptive labels describing consumable items and a plurality of relationships between pairs or groups of labels in the plurality of descriptive labels. In one embodiment, the descriptive labels of the food knowledge graph 230 at least include generic consumable names, but may include any other type of descriptive label discussed above with respect to FIGS. 4A-4E or any other useful descriptive labels not discussed above. Furthermore, the plurality of relationships of the food knowledge graph 230 may include any of the relationship types discussed above with respect to FIGS. 4A-4E, as well as any other useful relationship type not discussed above. In some embodiments, the processor circuitry/logic 204 is configured to operate the database 220 to store the food knowledge graph 230 in the form of one or more lists or tables that define a data tree or data web in which the descriptive labels comprise the nodes of the tree or web and the relationships comprise the connections between the nodes of the tree or web (for example, as illustrated in FIGS. 4A-4E). In one embodiment, the processor circuitry/logic 204 is configured to operate the database 220 to store the food knowledge graph 230 in the form of a reduced number of self-referential lists or tables, possible a single self-referential list or table, that define all of the labels and relationships that form the data tree or data web. In some embodiments, the processor circuitry/logic 204 is configured to operate the database 220 to store the labels and/or relationships as a list or table of triplets formed as, for example, [label_ID1, relationship_type, label_ID2] where label_ID1 is a first descriptive label or reference thereto, label_ID2 is a second descriptive label or reference thereto, and relationship_type indicates the nature of the relationship. However, the food knowledge graph can take any other suitable form.

The method 700 continues with a step of storing a plurality of consumable records, each consumable record including at least a descriptive string regarding a consumable item and each consumable record being associated with at least one label in the in the plurality of labels (block 720). Particularly, as discussed above, the processing circuitry/logic 204 of the server 200 is configured to maintain a consumable records database 224 in the memory 206. Each consumable record comprises a plurality of data fields that relate to a particular consumable item, including at least one description field have a descriptive string. In some embodiments, many, if not all, of consumable records 224 are created by users of the health tracking system 100 and have at least one user-generated text description field (e.g., the item description and brand description strings, discussed elsewhere herein). In addition, each consumable record is associated with one or more descriptive labels of the food knowledge graph 230. Particularly, in some embodiments, each consumable record includes one or more supplemental fields having references to descriptive labels of the food knowledge graph 230. As discussed in more detail with respect to FIG. 6C, some exemplary supplemental fields having references to descriptive labels of the food knowledge graph 230 may include fields for a standardized generic consumable name, a consumable category, a standardized brand name, a brand name category, dietary substitutes, included ingredients, included allergens, flavors, a type of cuisine, dietary restriction compliance, and other miscellaneous useful descriptive labels. In one embodiment, the supplemental fields were generated according to the method 500 or some similar labeling process.

The method 700 continues with a step of receiving a search string from the health tracking device of the user (block 730). Particularly, the processing circuitry/logic 204 of the system server 200 is configured to operate the network communications module 212 to receive a search string from a health tracking device 110, such as the smartphone 110A (e.g., "mac n cheese" in the example of FIG. 8A). In at least one embodiment, the processor 308 of one of the health tracking device 110 is configured to execute instructions of the client-side health tracking application 316 to enable a user to enter a search string, which will be used as the search string. The processor 308 is configured to operate the transceivers 312 to transmit the search string to the system server 200. The processing circuitry/logic 204 of the system server 200 is configured to operate the network communications module 212 to receive the search string from the health tracking device 110.

The method 700 continues with a step of matching the search string to at least one first label in the plurality of labels (block 740). Particularly, the processor circuitry/logic 204 is configured to execute a search labeling process of the health tracking application 218 to match the search string with one or more descriptive labels of the food knowledge graph 230. The search labeling process is essentially similar to, and possibly the same as, the food labeler 600 described above. The search labeling process is configured to, when executed by the processor circuitry/logic 204, match the search string with one or more descriptive labels of the food knowledge graph 230 and output a one or more matched labels. In one embodiment, the search labeling process is configured to compare the text of the search string with the labels and match the search string to the most similar label(s) of the food knowledge graph 230 or to all label(s) of the food knowledge graph 230 having at least a threshold level of similarity. In some embodiments, rather than using a rules-based text comparison, the search labeling process is configured to, when executed by the processor circuitry/logic 204, instead use a machine learning model to match the search string to labels of the food knowledge graph 230.

In some embodiments, the search labeling process is configured to, when executed by the processor circuitry/logic 204, match the search string only to a single most similar descriptive label, which might be a generic consumable name, a branded consumable, a brand name, a category of consumables, or another of the other types of labels described herein. For example, if the search string is "mac n cheese," as in the example of FIG. 8A, the processor circuitry/logic 204 might match the search string to the generic consumable name label "macaroni and cheese." Similarly, if the search string is "fruit," the processor circuitry/logic 204 might match the search string to the category of consumables label "fruit." However, in some embodiments, the search labeling process is configured to, when executed by the processor circuitry/logic 204, match the search string several labels in a similar manner as the food labeler 600. For example, if the search string is "mac n cheese," as in the example of FIG. 8A, the processor circuitry/logic 204 might match the search string to the generic consumable name label "macaroni and cheese," as well as the category of consumables label "pasta," or other related descriptive labels of the food knowledge graph 230. Additionally, for example, if the search string is "kraft mac n cheese," the processor circuitry/logic 204 might match the search string to the most similar generic consumable name label "macaroni and cheese" and to the most similar brand name label "Kraft®."

The method 700 continues with steps of generating a list of consumable records including consumable records in the plurality of consumable records that are associated with the at least one first label to which the search string was matched (block 750) and providing the list of consumable records to the health tracking device as search results (block 760). Particularly, the processor circuitry/logic 204 is configured to generate a list of consumable records from the consumable records 224 in the database 220 that are associated with and/or have the label(s) that was matched to the search string. The processor circuitry/logic 204 is configured to operate the network communications module 212 to transmit the generated list of consumable records to the health tracking device 110, such as the smartphone 110A, from which the search string was received. The processor 308 of the respective health tracking device 110 is configured to present the list of consumable records to the user as search results via a search results screen of a graphical user interface on the display screen 302.

Figure 8B:
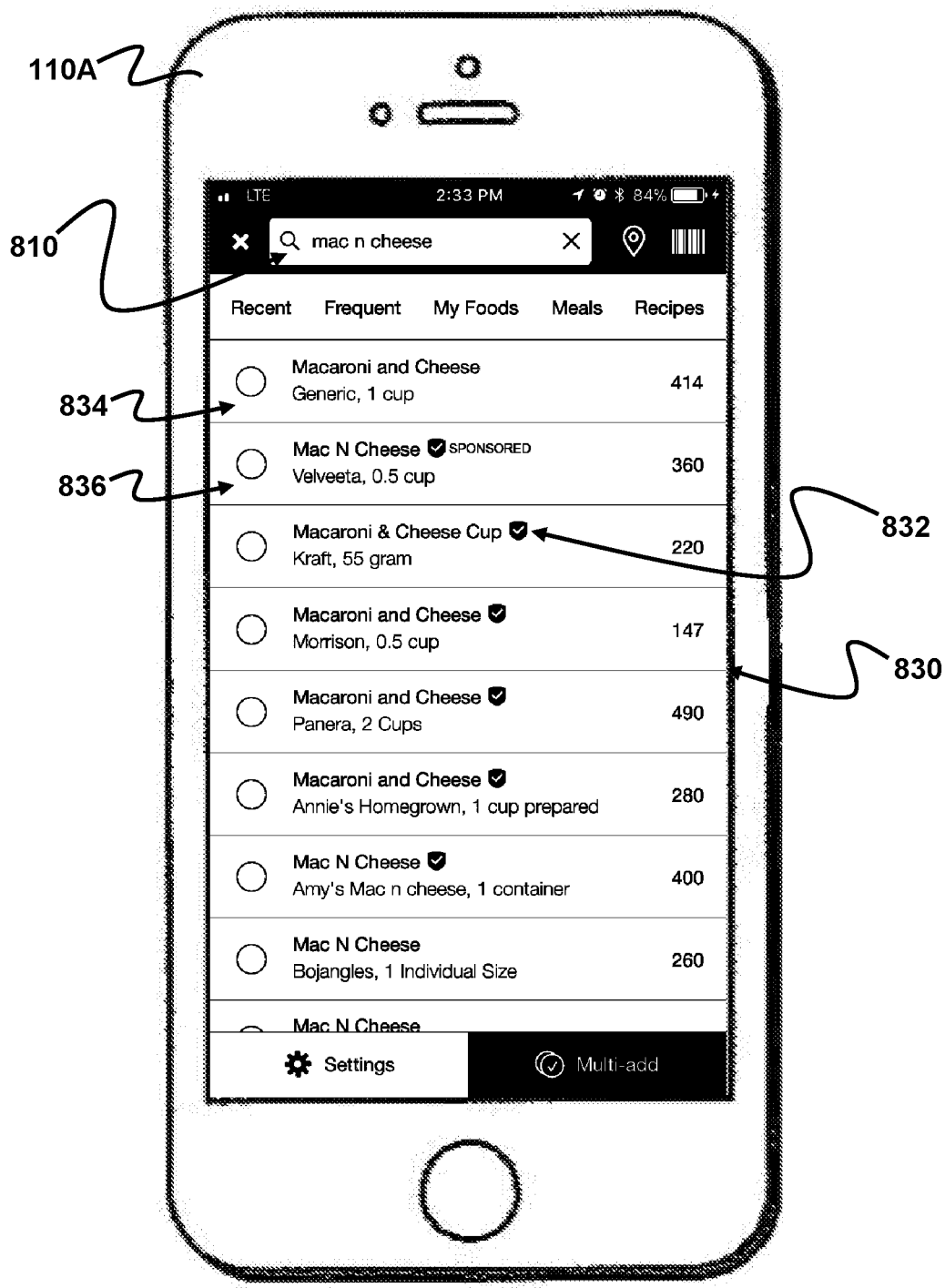
FIG. 8B shows an exemplary graphical user interface in which search results are populated using the food knowledge graph.

FIG. 8B shows an exemplary graphical user interface displayed on the smartphone 110A, in which a search of the consumable records 224 was performed by matching the search string to the food knowledge graph 230. As in the example of FIG. 8A, a user has entered the search string "mac n cheese" into a search window 810 of the graphical user interface. Improved search results 830 are displayed on the graphical user interface. The search results 830 only comprise consumable records that are associated with the generic consumable name label "macaroni and cheese" to which the search string was matched. Accordingly, the search results 830 only include consumable records that are relevant to the search string, and implicitly exclude records which are only superficially relevant due to containing similar words in their text descriptions (e.g., consumable records for macaroni noodles or consumable records for cheese).

In some embodiments, the ranking of the list of consumable records may be in accordance with the comparative popularity of each of the records, or by some other ranking method. Particularly, in some embodiments, each consumable record in the database 220 may be assigned a popularity score based on how frequently the consumable record is logged by users of the health tracking system 100. In at least one embodiment, the consumable records associated with the matched descriptive labels are ranked in the list according to their respective popularity score. In other embodiments, other scores may be assigned to consumable records and also used to rank the list of records, such as an accuracy or quality score. In addition some consumable records in the database 220 that are of high quality and accuracy may be automatically or manually marked as "verified" records by an administrator of the database 220 (indicated by a check mark 832 in the graphical user interface of FIG. 8B). These verified records may be automatically ranked higher in the list of consumable records that are provided as search results.

In some embodiments, each generic consumable name label and/or branded consumable name in the food knowledge graph 230 is associated with a particular consumable record that is considered to be the canonical consumable record or official consumable record for the respective generic consumable item and/or branded consumable item. In some embodiments, each particular combination a generic consumable name label and a brand name label may be associated with a canonical branded consumable record. In one embodiment, if the search string is matched to a generic consumable name label, but is not matched to any brand name labels or branded consumable name labels, then the processor circuitry/logic 204 is configured to provide the canonical generic consumable record at the top of the generated list of consumable records. In the example of FIG. 8B, the search string was matched to the "macaroni and cheese" generic consumable name label, but is not matched to any brand name labels or branded consumable name labels. Accordingly, a canonical record 834 having item description "Macaroni and Cheese" and brand description "Generic" is automatically provided at the top of the search results 830. Similarly, if a search string is matched to a generic consumable name label and a brand name label, the processor circuitry/logic 204 is configured to provide the canonical consumable record corresponding to that particular combination a generic consumable name label and a brand name label.

In some embodiments, if the search string is matched to a generic consumable name label, particularly if the search string is also not matched to any particular brand name labels or branded consumable name labels, then the processor circuitry/logic 204 is also configured to provide the most popular branded consumable records in the database 220 that are associated with matched generic consumable name label, as determined based on their respective popularity scores. For example, in the example of FIG. 8B, the search string was matched to the "macaroni and cheese" generic consumable name label, but is not matched to any brand name labels or branded consumable name labels. Accordingly, as shown in FIG. 8B, popular consumable records from the brands "Velveta," "Kraft," "Morrison," "Panera," "Annie's Homegown," "Amy's," and "Bojangles" are automatically provided in the search results 830, below the canonical generic consumable record 834.

In some embodiments, the processor circuitry/logic 204 is configured to operate the database 220 to store a list of sponsored consumable records and/or to mark a certain subset of the consumable records 224 as being sponsored. In one embodiment, the list of sponsored consumable records is managed by an administrator of the health tracking system 100. After matching the search string to a descriptive label of the food knowledge graph 230, the processor circuitry/logic 204 is configured to identify whether any of the sponsored consumable records are associated with the matched descriptive label. If so, the processor circuitry/logic 204 is configured to automatically include the sponsored consumable records associated with the matched descriptive label in the generated list. For example, as shown in FIG. 8B, a sponsored consumable record 836 was associated with the generic consumable name label "macaroni and cheese" and was automatically included in the search results 830.

In some embodiments, after generating the list of consumable records to be presented as search results to the user, the processor circuitry/logic 204 is configured to compare the labels with which each of the consumable records in list is associated. If two consumable records in the list are associated with exactly the same set of labels, then the processor circuitry/logic 204 is configured to exclude one of them from the list. For example, if two records are associated with the same generic consumable name label and the same brand name label, there is an implication that the two records are both for the same brand of the same consumable item, and thus are duplicative of one another. In other embodiments, other rules for identifying and excluding duplicative consumable records based on the associated labels can be utilized.

The method 700 also enables the user to search in a more diverse manner than could be accomplished with only a conventional text-comparison based search. Particularly, if a user enters the search string "fruit," a text-comparison based search would simply yield an assortment of consumable records that happen to have the word "fruit" in their item description or brand description (e.g. "Fruit Roll Up®" or "Mixed Fruit Cup"). However, in the method 700, the search string "fruit" would be matched to the category of consumables label "fruit." In some embodiments, when a search string matches best to a non-consumable name label, such as a category label, a brand name label, an allergen label, a dietary restriction label, or a flavor label, the processor circuitry/logic 204 is configured to generate the list of consumable records with the most popular consumable records associated with the non-consumable name label. In one embodiment, the list is generated with the most popular generic consumable records associated with the non-consumable name label. For example, if the search string matches to the category of consumables label "fruit," then the search results may include the most popular generic consumable records associated with the category of consumables label "fruit" (e.g., generic records for an apple, orange, watermelon, lemon, strawberry, etc) Similarly, if the search string matches to the cuisine label "Italian," then the search results may include the most popular consumable records associated with the cuisine label "Italian," (e.g., records for various types of pasta, pizza, etc.).

Figure 9:
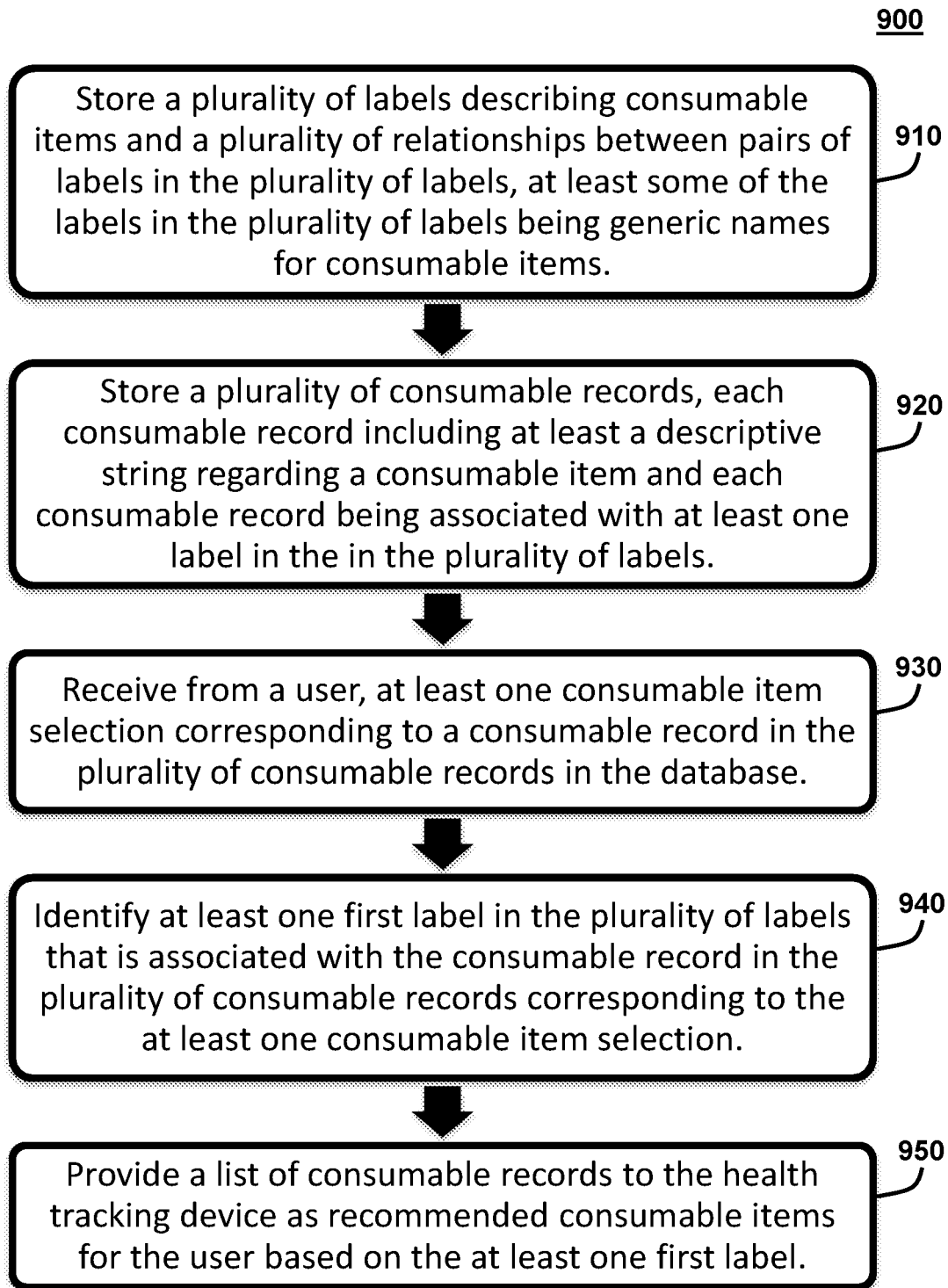
FIG. 9 shows a method of operating the health tracking system to provide improved recommendations using the food knowledge graph.

FIG. 9 shows a method 900 of operating the health tracking system 100 to provide improved recommendations using the food knowledge graph 230. Particularly, the method 900 utilizes the food knowledge graph 230, the additional information and/or metadata generated therewith, to provide recommendations based on a selection of one or more consumable records by a user. The method 900 improves the functioning of the system server 200 by enabling the processor circuitry/logic 204 to generate a list of recommended consumable records that are more relevant than would be provided based only on text-comparison based determinations of recommended consumable records.

The method 900 begins with a step of storing a plurality of labels describing consumable items and a plurality of relationships between pairs of labels in the plurality of labels, at least some of the labels in the plurality of labels being generic names for consumable items (block 910). Particularly, with respect to the embodiments disclosed in detail herein, the processor circuitry/logic 204 of the system server 200 is configured to operate the database 220 to store the food knowledge graph 230. The food knowledge graph 230 comprises a plurality of descriptive labels describing consumable items and a plurality of relationships between pairs or groups of labels in the plurality of descriptive labels. In one embodiment, the descriptive labels of the food knowledge graph 230 at least include generic consumable names, but may include any other type of descriptive label discussed above with respect to FIGS. 4A-4E or any other useful descriptive labels not discussed above. Furthermore, the plurality of relationships of the food knowledge graph 230 may include any of the relationship types discussed above with respect to FIGS. 4A-4E, as well as any other useful relationship type not discussed above. In some embodiments, the processor circuitry/logic 204 is configured to operate the database 220 to store the food knowledge graph 230 in the form of one or more lists or tables that define a data tree or data web in which the descriptive labels comprise the nodes of the tree or web and the relationships comprise the connections between the nodes of the tree or web (for example, as illustrated in FIGS. 4A-4E). In one embodiment, the processor circuitry/logic 204 is configured to operate the database 220 to store the food knowledge graph 230 in the form of a reduced number of self-referential lists or tables, possible a single self-referential list or table, that define all of the labels and relationships that form the data tree or data web. In some embodiments, the processor circuitry/logic 204 is configured to operate the database 220 to store the labels and/or relationships as a list or table of triplets formed as, for example, [label_ID1, relationship_type, label_ID2] where label_ID1 is a first descriptive label or reference thereto, label_ID2 is a second descriptive label or reference thereto, and relationship_type indicates the nature of the relationship. However, the food knowledge graph can take any other suitable form.

The method 900 continues with a step of storing a plurality of consumable records, each consumable record including at least a descriptive string regarding a consumable item and each consumable record being associated with at least one label in the in the plurality of labels (block 920). Particularly, as discussed in above, the processing circuitry/logic 204 of the server 200 is configured to maintain a consumable records database 224 in the memory 206. Each consumable record comprises a plurality of data fields that relate to a particular consumable item, including at least one description field have a descriptive string. In some embodiments, many, if not all, of consumable records 224 are created by users of the health tracking system 100 and have at least one user-generated text description field (e.g., the item description and brand description strings, discussed elsewhere herein). In addition, each consumable record is associated with one or more descriptive labels of the food knowledge graph 230. Particularly, in some embodiments, each consumable record includes one or more supplemental fields having references to descriptive labels of the food knowledge graph 230. As discussed in more detail with respect to FIG. 6C, some exemplary supplemental fields having references to descriptive labels of the food knowledge graph 230 may include fields for a standardized generic consumable name, a consumable category, a standardized brand name, a brand name category, dietary substitutes, included ingredients, included allergens, flavors, a type of cuisine, dietary restriction compliance, and other miscellaneous useful descriptive labels. In one embodiment, the supplemental fields were generated according to the method 500 or some similar labeling process.

The method 900 continues with a step of receiving from a user, at least one consumable item selection corresponding to a consumable record in the plurality of consumable records in the database (block 930). Particularly, the processing circuitry/logic 204 of the system server 200 is configured to operate the network communications module 212 to consumable item selection corresponding to a consumable record in the database from a health tracking device 110, such as the smartphone 110A (e.g., "mac n cheese" in the example of FIG. 8A). In at least one embodiment, the processor 308 of one of the health tracking device 110 is configured to execute instructions of the client-side health tracking application 316 to enable a user to view the details of the various consumable records 224 in in the database 220, as well as add individual consumable records to a food log or diary of the user. As used herein, a "consumable item selection" refers to an interaction of the user with one or more particular consumable records via a respective health tracking device 110, such as pressing or clicking on a consumable record in a list of consumable records to view the details of an individual consumable record, selecting one or more particular consumable records from a list of consumable records to log them to a food log or diary, or any other request from the health tracking device 110 regarding one or more particular consumable records in the databases 220. The processor 308 is configured to operate the transceivers 312 to transmit, to the system server 200, a request or message indicating a selection of a consumable record. The processing circuitry/logic 204 of the system server 200 is configured to operate the network communications module 212 to receive the request or message indicating a selection of a consumable record from the health tracking device 110. If the request or message indicates that the user would like to view the details of a particular consumable record, the processing circuitry/logic 204 may be configured to operate the network communications module 212 to transmit the details of the particular consumable record. Likewise, if the request or message indicates that the user would like to log the particular consumable record to a food log or diary, the processing circuitry/logic 204 may be configured to update the food log or diary based on the selected consumable record.

In at least one embodiment, the processor 308 of one of the health tracking device 110 is configured to execute instructions of the client-side health tracking application 316 to enable a user to request recommendations of consumable records from the system server 200. The processor 308 is configured to operate the transceivers 312 to transmit, to the system server 200, a recommendations request indicating that that the user wishes to receive recommendations. In some embodiments, the recommendations request may indicate that the user wishes to receive recommendations that are similar to, alternatives to, or substitutes of a particular selected consumable record. In some embodiments, the recommendations request may indicate that the user wishes to receive recommendations based on the types of consumables that they have previously added to their food log or diary. The processing circuitry/logic 204 of the system server 200 is configured to operate the network communications module 212 to receive the recommendations request from the health tracking device 110.

The method 900 continues with steps of identifying at least one first label in the plurality of labels that is associated with the consumable record in the plurality of consumable records corresponding to the at least one consumable item selection (block 940) and providing a list of consumable records to the health tracking device as recommended consumable items for the user based on the at least one first label (block 950). Particularly, the processing circuitry/logic 204 of the system server 200 is configured to identify which descriptive labels of the food knowledge graph 230 are associated with the consumable record(s) corresponding to the received consumable item selection, in response to receiving the consumable item selection and/or in response to receiving a recommendations request. Next, the processor circuitry/logic 204 is configured to generate a list of consumable records from the consumable records 224 in the database 220 based on the identified set of labels associated with the selected consumable record(s). The processor circuitry/logic 204 is configured to operate the network communications module 212 to transmit the generated list of consumable records to the health tracking device 110, such as the smartphone 110A, from which the consumable item selection or recommendations request was received. The processor 308 of the respective health tracking device 110 is configured to present the list of consumable records to the user as recommendations via a recommendations screen of a graphical user interface on the display screen 302.

Figure 10A:
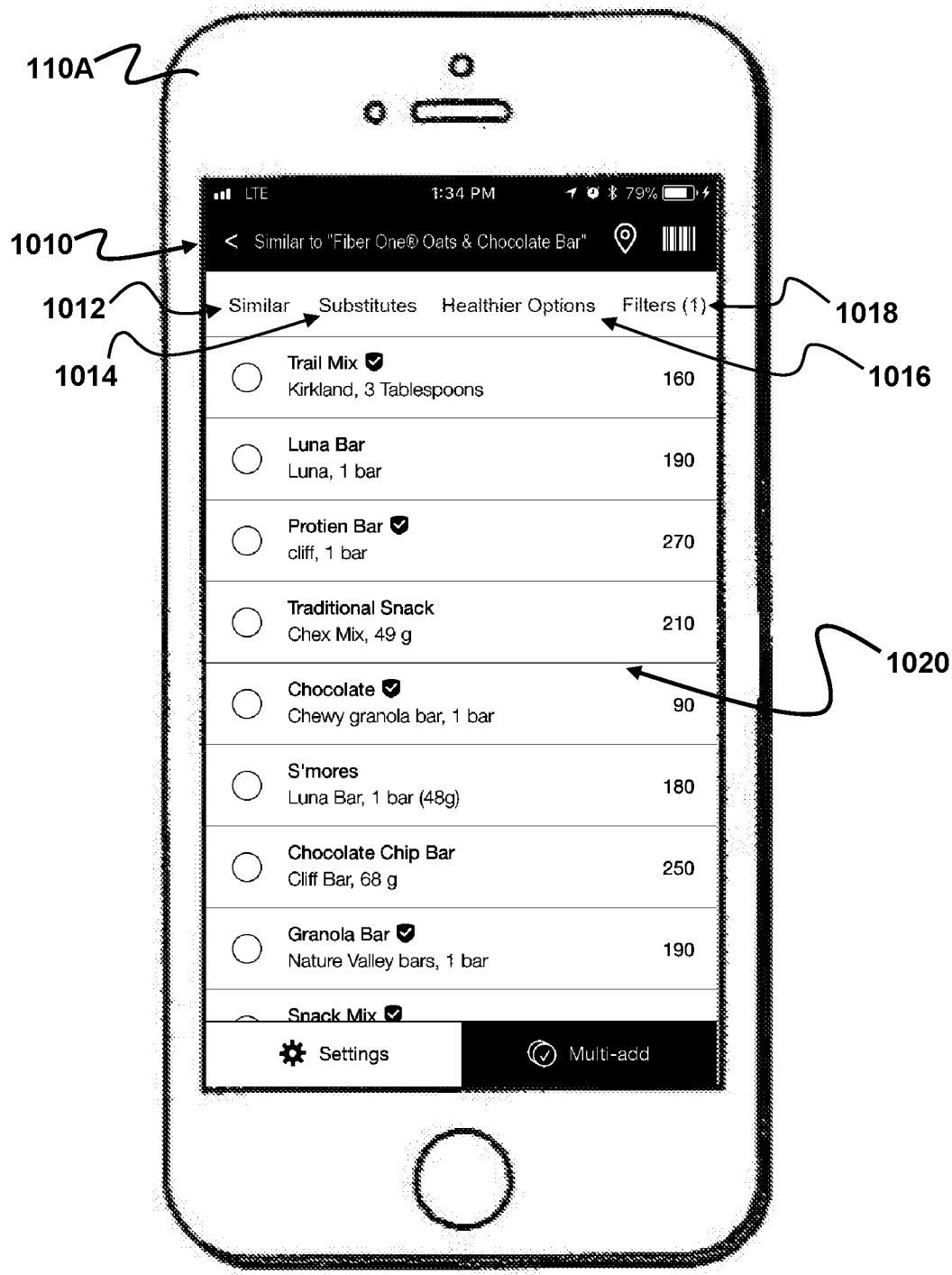
FIG. 10A shows an exemplary graphical user interface in which recommendations of similar consumables are provided using the food knowledge graph.

In at least one embodiment, in response to a recommendations request with respect to a particular consumable item selection, the processor circuitry/logic 204 is configured to generate a list of consumable records that are similar to, substitutes of, and/or alternatives the selected consumable record based on based the identified set of labels associated with the particular selected consumable record. FIG. 10A shows an exemplary graphical user interface displayed on the smartphone 110A, in which recommendations of similar consumable records are provided using the food knowledge graph 230. Particularly, a user selected a consumable record with the item description "Fiber One® Oats & Chocolate Bar" and requested recommendation of consumable records from the databases 220 that are similar to the selected consumable record by pressing a similar option 1012. The graphical user interface shows a title 1010 indicating the nature of the recommendations (e.g., 'Similar to "Fiber One® Oats & Chocolate Bar"') and a list 1020 of recommended consumable records. In the example, the processor circuitry/logic 204 identified that the selected consumable was associated with, for example, the generic consumable name "granola bar," the category of consumables "on-the-go snacks," and the ingredient names "oats," "granola," and "chocolate." As can be seen, the list 1020 includes consumable records for various other on-the-go snacks that are similar to the "Fiber One® Oats & Chocolate Bar" consumable record.

To generate a list of recommended consumable records that are similar to a particular consumable record, the processor circuitry/logic 204 is configured to identify the descriptive labels associated with the particular consumable record, and include consumable records in the list that are associated with a similar set of descriptive labels. In one embodiment, the processor circuitry/logic 204 is configured to included consumable records in the list only if they are associated with a minimum threshold amount of the same descriptive labels as the particular consumable record (e.g., at least 75% overlap in the associated labels). In one embodiment, the processor circuitry/logic 204 is configured to included consumable records in the list only if they are associated with a same category of consumables label as the particular consumable record. In one embodiment, the processor circuitry/logic 204 is configured to exclude consumable records that are associated with exactly the same set of labels as the selected consumable record (i.e., 100% overlap in the associated labels), to avoid recommending duplicative records or minor variants of the selected consumable record.

In some embodiments, a recommendation request may include an option or selection to show consumable records which are dietary substitutes to a selected consumable record. Particularly, the graphical user interface of FIG. 10A includes a substitutes option 1014, which can be pressed by the user. In response to the user pressing the substitutes option 1014, the processor 308 of the health tracking device 110 is configured to transmit a recommendations request indicating that the user wishes to receive recommendations of substitutes. When generating the list of recommended consumable records, the processor circuitry/logic 204 is configured to only include consumable records which are dietary substitutes of the selected consumable record, as defined by food knowledge graph 230. Depending on how the food knowledge graph 230 defines substitutes, the generated list of recommended substitute consumable records may require much more narrow similarity, as opposed to the recommendation of merely "similar" consumable records.

In some embodiments, a recommendation request may include an option or selection to show consumable records which are healthier alternatives to a selected consumable record. Particularly, the graphical user interface of FIG. 10A includes a healthier option 1016, which can be pressed by the user. In response to the user pressing the healthier option 1016, the processor 308 of the health tracking device 110 is configured to transmit a recommendations request indicating that the user wishes to receive recommendations of healthier alternatives. In some embodiments, at least some of the consumable records 224 in the database 220 each have a health score associated therewith, which is determined based on the nutritional information of the respective consumable record. When generating the list of recommended consumable records, the processor circuitry/logic 204 is configured to only include consumable records which are associated with a similar set of descriptive labels, but have a higher health score. In other embodiments, the processor circuitry/logic 204 is configured to populate the list of recommended consumable records based on some other method of evaluating the healthiness of the consumable records.

In some embodiments, a recommendation request may include options or selections for filtering the list of recommended consumable records, such as an option or selection to filter out any consumable records associated with a particular allergen. Particularly, the graphical user interface of FIG. 10A includes a filters option 1018, which can be pressed by the user to provide a menu of filter selections that can be selected by the user to filter the recommendations in various ways. In response to the user pressing the filters option 1018 and selecting a filter, the processor 308 of the health tracking device 110 is configured to transmit a recommendations request indicating that the user wishes to filter the recommendations of consumable records according to the selected filter. In one example, in response to the recommendations request including an allergen filter selection, the processor circuitry/logic 204 is configured to exclude consumable records from the list of recommended consumable records that are associated with the allergen, based on the food knowledge graph 230.

In some embodiments, a recommendation request may include an option or selection to show consumable records having the same brand as a selected consumable record. Particularly, when generating the list of recommended consumable records, the processor circuitry/logic 204 is configured to only include consumable records which are associated with the same brand label as the selected consumable record.

Figure 10B:
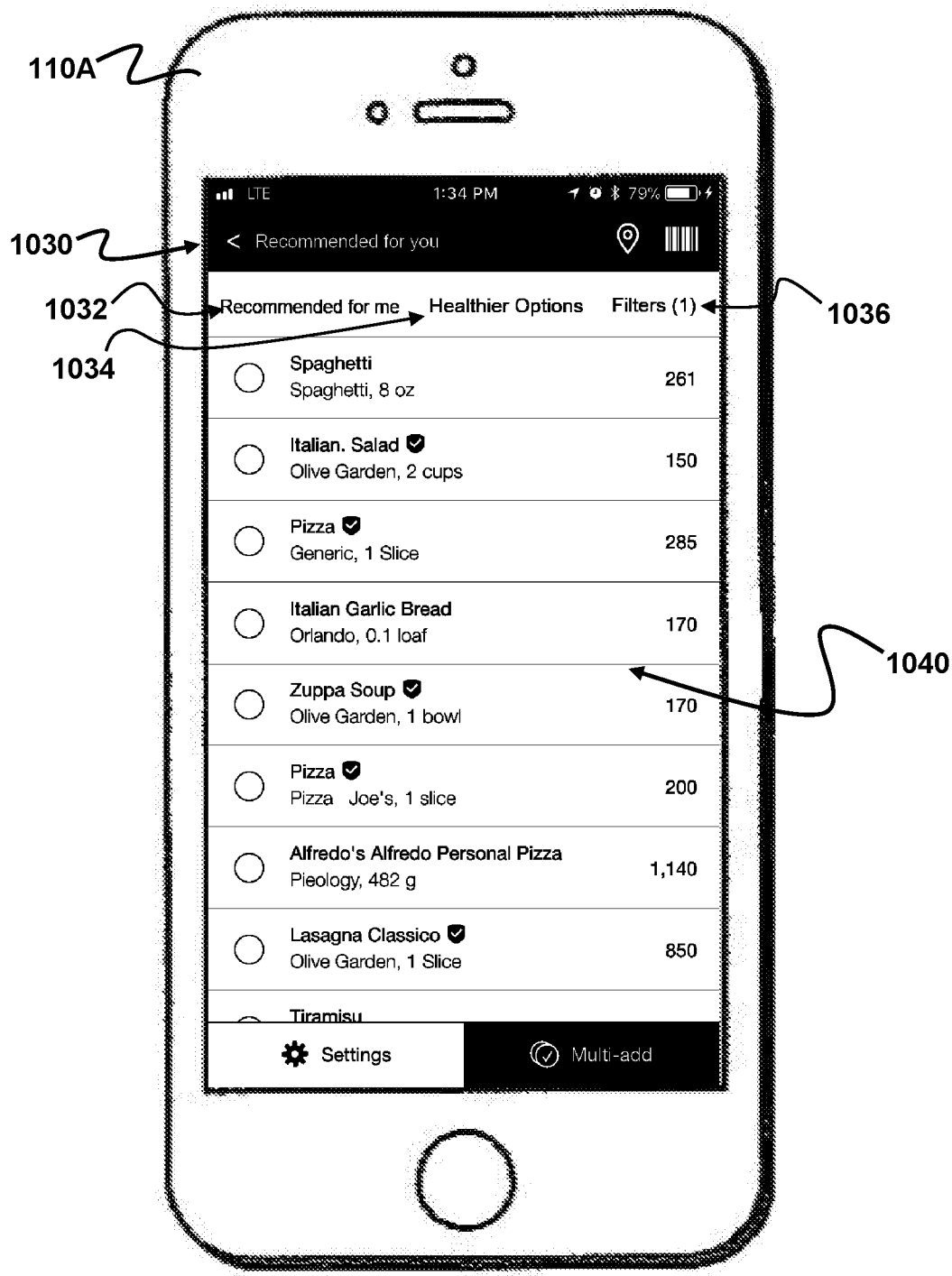
FIG. 10B shows an exemplary graphical user interface in which user-specific recommendations of consumables are provided using the food knowledge graph.

In at least one embodiment, in response to a recommendations request indicating that a user wishes to receive recommendations of consumable records based on the types of consumables that they have previously added to their food log or diary, the processor circuitry/logic 204 is configured to generate a list of consumable records that are similar to, substitutes of, and/or alternatives to the selected consumable records previously added to their food log or diary. FIG. 10B shows an exemplary graphical user interface displayed on the smartphone 110A, in which user-specific recommendations of consumables are provided using the food knowledge graph. The graphical user interface shows a title 1030 indicating the nature of the recommendations (e.g., 'Recommended for you'). A user has selected that he or she would like to receive recommendations of consumable records from the databases 220 based on the types of consumables that they have previously added to their food log or diary by pressing a recommended for me option 1032. In response to the selection, the processor 308 of the health tracking device 110 is configured to transmit a recommendations request indicating that the user wishes to receive recommendations of consumable records based on the types of consumables that they have previously added to their food log or diary.

In at least one embodiment, the processor circuitry/logic 204 is configured to generate a user dietary profile based on all of the consumable records that the user has previously added to their food log or diary, or based on the consumable records that the user has previously added to their food log or diary within a predetermined time period (e.g. the last six months). The processor circuitry/logic 204 is configured to identify, for each consumable record added to their food log or diary, which descriptive labels of the food knowledge graph 230 are associated therewith. Next, the processor circuitry/logic 204 is configured to calculate, for each descriptive label associated with the previously logged consumable records, a frequency at which the user has logged consumable records associated the respective label. These calculated frequencies and/or percentages form a user profile for the user from which recommendations of further consumable records can be made.

Returning to the example of FIG. 10B, the graphical user interface shows a list 1040 of recommended consumable records that are similar to consumable records that the user previously added to their food log or diary. Based the labels associated with the previously logged consumable records, the processor circuitry/logic 204 calculated that, for example, 50% of the consumable records logged by the user are associated with the "Italian" cuisine label, 15% of the consumable records logged by the user are associated with the "pizza" generic consumable name label, 20% of the consumable records logged by the user are associated with the "pasta" generic consumable name label, etc. As a result, the list 1040 of recommended consumable records includes several consumable records having similar associated descriptive labels to that of the user's dietary profile.

To generate a list of recommended consumable records based on those that the user has previously added to their food log or diary, the processor circuitry/logic 204 is configured to identify a subset of the descriptive labels that are most frequently associated with consumable records that the user has previously added to their food log or diary. When generating the list of recommended consumable records, the processor circuitry/logic 204 is configured to include consumable records that are associated with the most frequent labels. In one embodiment, the processor circuitry/logic 204 is configured to include consumable records in the list only if they are associated with a minimum threshold amount of the identified subset of the most frequent labels (e.g., at least 10% overlap with the most frequent labels).

In some embodiments, a recommendation request may include an option or selection to show consumable records which are healthier alternatives to a selected consumable record. Particularly, the graphical user interface of FIG. 10B includes a healthier option 1034, which can be pressed by the user. In response to the user pressing the healthier option 1034, the processor 308 of the health tracking device 110 is configured to transmit a recommendations request indicating that the user wishes to receive recommendations of healthier alternatives. In some embodiments, at least some of the consumable records 224 in the database 220 each have a health score associated therewith, which is determined based on the nutritional information of the respective consumable record. When generating the list of recommended consumable records, the processor circuitry/logic 204 is configured to only include consumable records which are associated with a similar set of descriptive labels as the most frequent labels, but have a higher health score. In other embodiments, the processor circuitry/logic 204 is configured to populate the list of recommended consumable records based on some other method of evaluating the healthiness of the consumable records.

In some embodiments, a recommendation request may include options or selections for filtering the list of recommended consumable records, such as an option or selection to filter out any consumable records associated with a particular allergen. Particularly, the graphical user interface of FIG. 10B includes a filters option 1036, which can be pressed by the user to provide a menu of filter selections that can be selected by the user to filter the recommendations in various ways. In response to the user pressing the filters option 1036 and selecting a filter, the processor 308 of the health tracking device 110 is configured to transmit a recommendations request indicating that the user wishes to filter the recommendations of consumable records according to the selected filter. In one example, in response to the recommendations request including an allergen filter selection, the processor circuitry/logic 204 is configured to exclude consumable records from the list of recommended consumable records that are associated with the allergen, based on the food knowledge graph 230.

The herein described applications utilizing food knowledge graph 230 (e.g., the health tracking program 218 and/or health tracking application 316) improve the functioning of the processing circuitry/logic 204 and/or the processor 308, respectively or in combination by enabling it/them to provide more informative, efficient, and diverse user interactions with the consumable records 224 in the database 220. Particularly, the method 500 improves the functioning of the system server 200 by enabling the processor circuitry/logic 204 to utilize the structured knowledge defined by the food knowledge graph 230 to provided additional information and/or metadata which is stored in or referenced by consumable records, in addition to the user-generated information of the consumable records. Additionally, the method 700 improves the functioning of the system server 200 by enabling the processor circuitry/logic 204 to generate a list of consumable records based on search string that are more relevant than would be provided based only on text-comparison based searching. The method 900 improves the functioning of the system server 200 by enabling the processor circuitry/logic 204 to generate a list of recommended consumable records that are more relevant than would be provided based only on text-comparison based determinations of recommended consumable records. Finally, devices that are able to utilize the food knowledge graph 230 can operate more efficiently to respond to various other types of requests for consumable records from the database 220.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

Particularly, in some embodiments, a permanent copy of the programming instructions for individual ones of the aforementioned applications utilizing the food knowledge graph 230 (e.g., the health tracking program 218 and/or health tracking application 316) may be placed into permanent storage devices (such as e.g., the memory 206 and/or the memory 310) during manufacture thereof, or in the field, through e.g., a distribution medium (not shown), such as a compact disc (CD), or through communication interface 212, 304 from a distribution server (such as the server 200 and/or another distribution server). That is, one or more distribution media having an implementation of the agent program may be employed to distribute the agent and program various computing devices.

The foregoing detailed description of one or more exemplary embodiments of the health tracking system 100 has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method of operating a health tracking system, the method comprising:
    storing in a crowdsourced database of data records, a food knowledge graph defined by a data web comprised of a plurality of nodes and a plurality of connections between the nodes, wherein the nodes of the data web are defined by a plurality of labels describing consumable items and wherein the connections between the nodes are defined by a plurality of relationships between pairs of labels in the plurality of labels, at least some of the labels in the plurality of labels being generic names for consumable items, and wherein, for each pair of labels, one relationship is defined between a first label and a second label of said pair of labels, said one relationship identifying one of (i) the second label as an allergen of the first label, (ii) the second label as a substitute for the first label, and (iii) the second label as a flavor of the first label;
    receiving a data record comprising at least one descriptive string regarding a first consumable item from a first health tracking device;
    including the received data record within the crowdsourced database of data records;
    matching the at least one descriptive string to at least one first label of the pairs of labels in the plurality of labels by implementing a machine learning model in order to match the at least one descriptive string to the at least one first label of the pairs of labels in the plurality of labels;
    updating at least one first information field of the data record to associate the data record with the at least one first label to which the at least one descriptive string was matched;
    identifying at least one second label in the plurality of labels that is related to the at least one first label based on the plurality of relationships;
    updating at least one second information field of the data record to associate the data record with the identified at least one second label;
    receiving a request for data records in the crowdsourced database from a second health tracking device;
    matching the request for data records from the second health tracking device to the at least one first label or the at least one second label; and
    providing the data record having the updated at least one first information field and the at least one second information field to the second health tracking device in response to the request being matched to the at least one first label or the at least one second label, wherein said provided data record is displayed on the second health tracking device along with a menu allowing the user to select a first option for recommended similar items for the provided data record, a second option for recommended substitutes for the provided data record, and a third option for recommended healthier items in lieu of the displayed data record;
    after receiving a selection of the first option, generating a first list of one or more additional data records in the crowdsourced database that are associated with a first minimum threshold amount of same descriptive labels as the provided data record, and transmitting the first list to the second health tracking device by wireless transmission and immediately displaying the first list on the second health tracking device following receipt of the selection of the first option;

after receiving a selection of the second option, generating a second list of one or more additional data records in the crowdsourced database that are either (i) identified as substitutes for the provided data record in the food knowledge graph, or (ii) associated with a second minimum threshold amount of the same descriptive labels as the provided data record, wherein the second minimum threshold is greater than the first minimum threshold, and transmitting the second list to the second health tracking device by wireless transmission and immediately displaying the second list on the second health tracking device following receipt of the selection of the second option; and after receiving a selection of the third option, generating a third list of one or more additional data records in the crowdsourced database that are associated with a third minimum threshold amount of the same descriptive labels as the provided data record and also have a health score in the crowdsourced database that is greater than that of the provided data record, and transmitting the third list to the second health tracking device by wireless transmission and immediately displaying the third list on the second health tracking device following receipt of the selection of the third option.

2. The method according to claim 1 further comprising:
the at least one first label includes a first generic name in the plurality of labels; and
the method further comprises:
   updating a generic name field of the data record to associate the data record with the first generic name.

3. The method according to claim 1, wherein:
at least some of the labels in the plurality of labels are brand names;
the at least one first label includes a first brand name in the plurality of labels;
at least some of the relationships in the plurality of relationships indicate that a respective first generic name in the plurality of labels has a respective brand name in the plurality of labels; and
the updating further comprises updating a brand name field of the data record to associate the data record with the first brand name.

4. The method according to claim 1, wherein:
the at least one first label includes a first generic name in the plurality of labels;
at least some of the labels in the plurality of labels are categories of consumable items;
at least some of the relationships in the plurality of relationships indicate that a respective generic name in the plurality of labels is part of a respective category of consumable items in the plurality of labels; and
the method further comprises:
   identifying a category of consumable items that is related to the first generic name based on the plurality of relationships; and
   updating a category field of the data record to associate the data record with the identified category of consumable items.

5. The method according to claim 1, wherein:
the at least one first label includes a first generic name in the plurality of labels;
at least some of the relationships in the plurality of relationships indicate that a respective first generic name in the plurality of labels is a dietary substitute of a respective second generic name in the plurality of labels; and the method further comprises:
   identifying at least one second generic name that is a dietary substitute of the first generic name based on the plurality of relationships; and
   updating a substitute field of the data record to associate the data record with the identified at least one second generic name.

6. The method according to claim 1, wherein:
the at least one first label includes a first generic name in the plurality of labels;
at least one of the relationships in the plurality of relationships indicate that the first generic name in the plurality of labels is an ingredient of a second generic name in the plurality of labels; and
the method further comprises:
   identifying at least one second generic name that is an ingredient of the first generic name based on the plurality of relationships; and
   updating an ingredient field of the data record to associate the data record with the identified at least one second generic name.

7. The method according to claim 1, wherein:
the data record comprises a plurality of descriptive strings; and
the method further comprises:
   matching each descriptive string in the plurality of descriptive strings to at least one respective label in the plurality of labels; and
   updating for each descriptive string in the plurality of descriptive strings, at least one information field of the data record to associate the data record with the at least one respective label to which the respective descriptive string was matched.

8. The method according to claim 7, wherein:
the data record corresponds to a recipe and the plurality of descriptive strings thereof includes a recipe name string and a plurality of ingredient name strings; and
the method further comprises:
   matching the recipe name string to a generic name in the plurality of labels;
   matching each ingredient name string in the plurality of ingredient name strings to a generic name in the plurality of labels;
   updating a recipe type field of the data record to associate the data record with the generic name to which the recipe name string was matched; and
   updating an ingredient field of the data record to associate the data record with the generic names to which the plurality of ingredient name strings were matched.

9. A method of operating a health tracking system, the method comprising:
storing in a database of data records, a food knowledge graph defined by a data web comprised of a plurality of nodes and a plurality of connections between the nodes, wherein the nodes of the data web are defined by a plurality of labels describing consumable items and wherein the connections between the nodes are defined by a plurality of relationships between pairs of labels in the plurality of labels, at least some of the labels in the plurality of labels being generic names for consumable items, and wherein, for each pair of labels, one relationship is defined between a first label and a second label of said pair of labels, said one relationship identifying one of (i) the second label as an allergen of the first label, (ii) the second label as a substitute for the first label, and (iii) the second label as a flavor of the first label;

receiving a data record comprising at least one descriptive string regarding a first consumable item;

including the received data record within the database of data records;

matching the at least one descriptive string to at least one first label of the pairs of labels in the plurality of labels;

updating at least one first information field of the data record to associate the data record with the at least one first label to which the at least one descriptive string was matched;

identifying at least one second label in the plurality of labels that is related to the at least one first label based on the plurality of relationships;

updating at least one second information field of the data record to associate the data record with the identified at least one second label;

receiving a request for data records in the database from a health tracking device;

matching the request for data records from the health tracking device to the at least one first label or the at least one second label;

providing the data record having the updated at least one first information field and the at least one second information field to the health tracking device in response to the request being matched to the at least one first label or the at least one second label, wherein said provided data record is displayed on the health tracking device along with a menu allowing the user to select (i) a first option for recommended similar items for the provided data record, (ii) a second option for recommended substitutes for the provided data record, and (iii) a third option for recommended healthier items than the provided data record;

when a selection of the first option is received, generating a first list of one or more additional data records in the database that are associated with a first minimum threshold amount of same descriptive labels as the provided data record, and following generation of the first list, displaying the first list in real time on the health tracking device;

when a selection of the second option is received, generating a second list of one or more additional data records in the database that are either (i) identified as substitutes for the provided data record in the food knowledge graph, or (ii) associated with a second minimum threshold amount of the same descriptive labels as the provided data record, wherein the second minimum threshold is greater than the first minimum threshold, and following generation of the second list, displaying the second list in real time on the health tracking device; and when a selection of the third option is received, generating a third list of one or more additional data records in the database that are associated with a third minimum threshold amount of the same descriptive labels as the provided data record and also have a health score in the database that is greater than the provided data record, and displaying said third list in real time on the second health tracking device.

10. The method according to claim 9 wherein the at least one first label includes a first generic name in the plurality of labels, the method further comprising:

updating a generic name field of the data record to associate the data record with the first generic name.

11. The method according to claim 9, wherein:

the at least one first label includes a first generic name in the plurality of labels;

at least some of the labels in the plurality of labels are categories of consumable items;

at least some of the relationships in the plurality of relationships indicate that a respective generic name in the plurality of labels is part of a respective category of consumable items in the plurality of labels; and the method further comprises:

identifying a category of consumable items that is related to the first generic name based on the plurality of relationships; and updating a category field of the data record to associate the data record with the identified category of consumable items.

12. The method of claim 9, wherein matching the at least one descriptive string to at least one first label of the pairs of labels in the plurality of labels is accomplished by implementing a machine learning model in order to match the at least one descriptive string to at least one first label of the pairs of labels in the plurality of labels.

13. The method of claim 9, wherein:

the at least one first label includes a first generic name in the plurality of labels;

at least one of the relationships in the plurality of relationships indicate that the first generic name in the plurality of labels is an ingredient of a second generic name in the plurality of labels; and the method further comprises:

identifying at least one second generic name that is an ingredient of the first generic name based on the plurality of relationships; and updating an ingredient field of the data record to associate the data record with the identified at least one second generic name.

* * * * *